(12) United States Patent
Carlson et al.

(10) Patent No.: US 11,452,714 B2
(45) Date of Patent: Sep. 27, 2022

(54) ANTIBACTERIAL AGENTS INCLUDING HISTIDINE KINASE INHIBITORS

(71) Applicant: Regents of the University of Minnesota, Minneapolis, MN (US)

(72) Inventors: Erin E. Carlson, Minneapolis, MN (US); Manibarsha Goswami, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 119 days.

(21) Appl. No.: 16/615,585

(22) PCT Filed: May 23, 2018

(86) PCT No.: PCT/US2018/034118
§ 371 (c)(1),
(2) Date: Nov. 21, 2019

(87) PCT Pub. No.: WO2018/217884
PCT Pub. Date: Nov. 29, 2018

(65) Prior Publication Data
US 2020/0101048 A1 Apr. 2, 2020

Related U.S. Application Data

(60) Provisional application No. 62/509,968, filed on May 23, 2017.

(51) Int. Cl.
| | | |
|---|---|---|
| *A01N 43/04* | (2006.01) | |
| *A61K 31/70* | (2006.01) | |
| *A61K 31/428* | (2006.01) | |
| *A61K 31/52* | (2006.01) | |
| *A61K 31/7076* | (2006.01) | |

(52) U.S. Cl.
CPC .......... *A61K 31/428* (2013.01); *A61K 31/52* (2013.01); *A61K 31/7076* (2013.01)

(58) Field of Classification Search
None
See application file for complete search history.

(56) References Cited

U.S. PATENT DOCUMENTS

| | | |
|---|---|---|
| 2,385,224 A | 9/1945 | Newbery |
| 5,747,276 A | 5/1998 | Hoch et al. |
| 6,077,682 A | 6/2000 | Inouye et al. |
| 2003/0008841 A1 | 1/2003 | Devos et al. |
| 2005/0187389 A1 | 8/2005 | Milanov et al. |
| 2010/0190806 A1 | 7/2010 | Spichal et al. |
| 2014/0303112 A1 | 10/2014 | Chen et al. |

FOREIGN PATENT DOCUMENTS

| | | |
|---|---|---|
| EP | 1444982 | 8/2004 |
| WO | WO1993/14103 | 7/1993 |
| WO | WO2004/002999 | 1/2004 |
| WO | WO2006/040558 | 4/2006 |

OTHER PUBLICATIONS

Pandurangan et al. Der Pharma Chemica (2010), vol. 2(3), pp. 316-324.*
Bader et al., "Regulation of *Salmonella typhimurium* virulence gene expression by cationic antimicrobial peptides," Molecular Microbiology, vol. 50, No. 1, Oct. 2003, 12 pp.
Bern, et al., "Bacterial Histidine Kinases as Novel Antibacterial Drug Targets," ACS Chemical Biology, vol. 10, Jan. 2015, 12 pp.
Boibessot et al., "The Rational Design, Synthesis, and Antimicrobial Properties of Thiophene Derivatives That Inhibit Bacterial Histidine Kinases," Journal of Medicinal Chemistry, vol. 59, No. 19, Oct. 2016, 54 pp.
Cai et al., "The Effect of the Potential PhoQ Histidine Kinase Inhibitors on *Shigella flexneri* Virulence," PLoS One, vol. 6, No. 8, e23100, Aug. 2011, 14 pp.
Chamnongpol et al., "Acetyl Phosphate-dependent Activation of a Mutant PhoP Response Regulator that Functions Independently of its Cognate Sensor Kinase," Journal of Molecular Biology, vol. 300, No. 2, Jul. 2000, 15 pp.
Choi et al., "Acidic pH sensing in the bacterial cytoplasm is required for *Salmonella* virulence," Molecular Microbiology, vol. 101, No. 6, Jul. 2106, 15 pp.
Cui et al., "Contribution of vraSR and graSR Point Mutations to Vancomycin Resistance in Vancomycin-Intermediate *Staphylococcus aureus*," Antimicrobial Agents and Chemotherapy, vol. 53, No. 3, Mar. 2009, 4 pp.
Dong et al., "Sulfur(VI) Fluoride Exchange (SuFEx): Another Good Reaction for Click Chemistry," Angewandte Chemie International Edition, vol. 53, No. 36, Sep. 2014, 19 pp.
Dorr et al., "A cell wall damage response mediated by a sensor kinase/response regulator pair enables beta-lactam tolerance," Proceedings of the National Academy of Sciences of the United States of America, vol. 113, No. 2, Jan. 2016, 6 pp.
Eguchi et al., "Development of an Antivirulence Drug against *Streptococcus mutans*: Repression of Biofilm Formation, Acid Tolerance, and Competence by a Histidine Kinase Inhibitor, Walkmycin C," Antimicrobial Agents and Chemotherapy, vol. 55, No. 4, Apr. 2011, 10 pp.

(Continued)

*Primary Examiner* — Patrick T Lewis
(74) *Attorney, Agent, or Firm* — Shumaker & Sieffert, P.A.

(57) ABSTRACT

An example composition includes a therapeutically effective amount of a histidine kinase inhibitor. The histidine kinase inhibitor includes at least one of a 6-benzo[d]thiazol-2-amine derivative, a purine derivative, an adenine derivative, an adenine-sulfonyl fluoride derivative, a riluzole analog, a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative. An example technique for treating a bacterial infection includes administering a composition comprising a histidine kinase inhibitor to a patient.

15 Claims, 12 Drawing Sheets

(56) References Cited

OTHER PUBLICATIONS

Fields et al., "A *Salmonella* Locus That Controls Resistance to Microbicidal Proteins from Phagocytic Cells," Science, vol. 243, No. 4894, Feb. 1989, 4 pp.

Galan et al., "Virulence and vaccine potential of phoP mutants of *Salmonella typhimurium*," Microbial Pathogenesis, vol. 6, No. 6, Jun. 1989, 11 pp.

Galbusera et al., "Site-Specific Mutation of *Staphylococcus aureus* VraS Reveals a Crucial Role for the VraR-VraS Sensor in the Emergence of Glycopeptide Resistance," Antimicrobial Agents and Chemotherapy, vol. 55, No. 3, Mar. 2011, 13 pp.

Garcia Vescovi et al., "$Mg^{2+}$ as an Extracellular Signal: Environmental Regulation of *Salmonella* Virulence," Cell, vol. 84, Jan. 1996, 10 pp.

Gellatly et al., "The *Pseudomonas aeruginosa* PhoP-PhoQ Two-Component Regulatory System is Induced upon Interaction with Epithelial Cells and Controls Cytotoxicity and Inflammation," Infection and Immunity, vol. 80, No. 9, Sep. 2012, 10 pp.

Goodman et al., "A Signaling Network Reciprocally Regulates Genes Associated with Acute Infection and Chronic Persistence in *Pseudomonas aeruginosa*," Developmental Cell, vol. 7, Nov. 2004, 10 pp.

Goswami et al., "Bacterial Histidine Kinases as Targets for Development of Effective Antibiotics," Poster Presentation 2016 Chemistry Biology Interface Training Grant Symposium, May 2016, 1 pp.

Goswami et al., "Bacterial Histidine Kinases as Targets for Development of Effective Antibiotics," Poster Presentation the International Chemical Biology Society's 5th Annual Meeting, Oct. 2016, 1 pp.

Goswami et al., "Disarming the virulence arsenal of *Pseudomonas aeruginosa* by blocking two-component system signaling," Chemical Science, vol. 9, No. 37, Jul. 2018, 6 pp.

Goswami, et al., "Rational design of selective adenine-based scaffolds for inactivation of bacterial histidine kinases," Journal of Medicinal Chemistry, vol. 60, No. 19, Oct. 2017, 28 pp.

Groisman et al., "*Salmonella, typhimurium* phoP virulence gene is a transcriptional regulator," Proceedings of the National Academy of Sciences of the United States of America (PNAS), vol. 86, No. 18, Sep. 1989, 5 pp.

Guarnieri et al., "The Hsp90 Inhibitor Radicicol Interacts with the ATP-Binding Pocket of Bacterial Sensor Kinase PhoQ," Journal of Molecular Biology, vol. 379, No. 1, May 2008, 12 pp.

Haraga et al., "*Salmonellae* interplay with host cells," Nature Reviews Microbiology, vol. 6, No. 1, Jan. 2008, 14 pp.

Havlicek, et al., "Cytokinin-Derived Cyclin-Dependent Kinase Inhibitors: Synthesis and cdc2 Inhibitory Activity of Olomoucine and Related Compounds," Journal of Medicinal Chemistry, vol. 40, No. 4, Feb. 1997, 5 pp.

Himpins et al., "Molecular characterization of the mycobacterial SenX3-RegX3 two-component systems: evidence for autoregulation," Microbiology, vol. 146, No. 12, Dec. 2000, 8 pp.

Kraus et al., "The GraRS regulatory system controls *Staphylococcus aureus* susceptibility to antimicrobial host defenses," BMC Microbiology, vol. 8, No. 1, Jun. 2008, 5 pp.

Maruthamuthu, et al., "Synthesis, characterization and pharmacological studies of biologically active benzothiazole derivatives," World Journal of Pharmaceutical Research, vol. 3, No. 5, May 2014, 9 pp.

Miller et al., "A Two-component regulator)/ system (phoP phoQ) controls *Salmonella typhimurium* virulence," Proceedings of the National Academy of Sciences of the United States of America (PNAS), vol. 86, No. 13, Jul. 1989, 5 pp.

Morris et al., "Imaging and Analysis of *Pseudomonas aeruginosa* Swarming and Rhamnolipid Production," Applied and Environmental Microbiology, vol. 77, No. 23, Dec. 2011, 8 pp.

Moss et al., "The regulatory/ protein PhoP controls susceptibility to the host inflammatory-response in *Shigella flexneri*," Cellular Microbiology, vol. 2, No. 6, Dec. 2000, 10 pp.

Narayanan et al., "Sulfonyl fluorides as privileged warheads in chemical biology," Chemical Science, vol. 6, No. 5, Mar. 2015, 10 pp.

Neidig et al., TypA is involved in virulence, antimicrobial resistance and biofilm formation in *Pseudomonas aeruginosa*, BMC Microbiology, vol. 13, No. 1, Dec. 2013, 10 pp.

Oyston et al., "The Response Regulator PhoP is Important for Survival under Conditions of Macrophage-Induced Stress and Virulence in *Yersinia pestis*," Infection and Immunity, vol. 68, No. 6, Jun. 2000, 7 pp.

Palmer et al., Benzothiazolines as Antituberculous Agents, Journal of Medicinal Chemistry, vol. 14, No. 3, Mar. 1971, 4 pp.

Park et al., "Signal-specific temporal response by the *Salmonella* PhoP/PhoQ regulatory system," Molecular Microbiology, vol. 91, No. 1, Jan. 2014, 10 pp.

Payne et al. "Drugs for bad bugs: confronting the challenges of antibacterial discovery," Nature Reviews Drug Discovery, vol. 6, Jan. 2007, 12 pp.

Peterson, J.W., "Bacterial Pathogenesis," Chapter 7, Medical Microbiology, $4^{th}$ Edition, 1996, 14 pp. (Applicant points out, in accordance with MPEP 609.04(a), that the year of publication, 1996, is sufficiently earlier than the effective U.S. filing date, so that the particular month of publication is not in issue.).

Pfaffl, M.W., "A new mathematical model for relative quantification in real-time RT-PCR," Nucleic Acids Research, vol. 29, No. 1, May 2001, 6 pp.

Prost et al., "Activation of the Bacterial Sensor Kinase PhoQ by Acidic pH," Molecular Cell, vol. 26, No. 2, Apr. 2007, 10 pp.

Sakhtah et al., "Regulation of Phenazine Biosynthesis," Chapter 2, Microbial Phenazines: Biosynthesis, Agriculture and Health, 2013, 24 pp. (Applicant points out, in accordance with MPEP 609.04(a), that the year of publication, 1996, is sufficiently earlier than the effective U.S. filing date, so that the particular month of publication is not in issue.).

Schneider et al., "NIH Image to ImageJ: 25 years of image analysis," Nature Methods, vol. 9, No. 7, Jul. 2012, 5 pp.

Shin et al., "A Positive Feedback Loop Promotes Transcription Surge That Jump-Starts *Salmonella* Virulence Circuit," Science, vol. 314, No. 5805, Dec. 2006, 3 pp.

Silver, L.L., "Challenges of Antibacterial Discovery," Clinical Microbiology Reviews, vol. 24, No. 1, Jan. 2011, 39 pp.

Singh et al., "The resurgence of covalent drugs," Mature Reviews-Drug Discovery, vol. 10, No. 4, Apr. 2011, 11 pp.

Soncini et al., "Molecular Basis of the Magnesium Deprivation Response in *Salmonella typhimurium*: Identification of PhoP-Regulated Genes," Journal of Bacteriology, vol. 178, No. 17, Sep. 1996, 8 pp.

Stock et al., "Two-Component Signal Transduction," Annual Review of Biochemistry, vol. 69, No. Jul. 1, 2000, 35 pp.

Sun et al., "In the *Staphylococcus aureus* Two-Component System sae, the Response Regulator SaeR Binds to a Direct Repeat Sequence and DNA Binding Requires Phosphorylation by the Sensor Kinase SaeS," Journal of Bacteriology, vol. 192, No. 8, Apr. 2010, 17 pp.

Tremblay et al., "Improving the reproducibility of *Pseudomonas aeruginosa* swarming motility assays," Journal of Basic Microbiology, vol. 48, No. 6, Dec. 2008, 7 pp.

Velikova et al., "Putative histidine kinase inhibitors with antibacterial effect against multi-drug resistant clinical isolates identified by in vitro and in silico screens," Scientific Reports, vol. 6, Art. No. 26085, May 2016, 16 pp.

Wei, et al., "Adenosine analogs as inhibitors of tyrosyl-tRNA synthetase: Design, synthesis and antibacterial evaluation," Bioorganic & Medicinal Chemistry, vol. 23, No. 20, Oct. 2015, 10 pp.

Welsh et al., "Small Molecule Disruption of Quorum Sensing Cross-Regulation in *Pseudomonas aeruginosa* Causes Major and Unexpected Alterations to Virulence Phenotypes," Journal of the American Chemical Society, vol. 137, No. 4, Feb. 2015, 23 pp.

Wilke et al., "Activity-Based Probe for Histidine Kinase Signaling," Journal of the American Chemical Society, vol. 134, No. 22, Jun. 2012, 9 pp.

Wilke, et al., "Inactivation of Multiple Bacterial Histidine Kinases by Targeting the ATP-Binding Domain," ACS Chemical Biology, vol. 10, No. 1, Jan. 2015, 8 pp.

(56) References Cited

OTHER PUBLICATIONS

World Health Organization, article entitled "Antimicrobial resistance," retrieved from http://www.who.int/mediacentre/factsheets/fs194/en/ , dated Feb. 15, 2018, Downloaded Apr. 16, 2020, 7 pp.
International Preliminary Report on Patentability from International Application No. PCT/US2018/034118, dated Dec. 5, 2019, 9 pp.
International Search Report and Written Opinion of International Application No. PCT/US2018/034118, dated Sep. 12, 2018, 16 pp.

* cited by examiner

ANTIBACTERIAL AGENTS INCLUDING HISTIDINE KINASE INHIBITORS

This application is a National Stage application under 35 U.S.C. § 371 of PCT Application No. PCT/US2018/034118, entitled "ANTIBACTERIAL AGENTS INCLUDING HISTIDINE KINASE INHIBITORS" and filed on May 23, 2018, which claims the benefit of U.S. Provisional Patent Application No. 62/509,968, titled "ANTIBACTERIAL AGENTS INCLUDING HISTIDINE KINASE INHIBITORS" and filed May 23, 2017. The entire contents of application Nos. PCT/US2018/034118 and U.S. 62/509,968 are incorporated herein by reference.

GOVERNMENT RIGHTS

This invention was made with government support under OD008592 awarded by National Institutes of Health. The government has certain rights in the invention.

TECHNICAL FIELD

This disclosure relates to antibacterial agents, and in particular, to antibacterial agents including histidine kinase inhibitors.

BACKGROUND

Antimicrobial resistance (AMR) has become a global concern as new resistance mechanisms are continuously emerging, hindering the treatment of even relatively common infections. While antibiotics may be used to combat infections caused by bacteria, the prevalence of treatment based on antibiotics has led to antibiotic resistance. For example, certain strains of bacteria develop resistance to antibiotics by genetic mutation or by acquiring resistance from other strains or species. Antibiotic resistance (ABR) in particular has been increasing at an alarming rate as bacteria can become invulnerable to an antibiotic within four years of its discovery. Infections caused by antibiotic-resistant bacteria are more difficult to treat than infections caused by non-resistant bacteria. The administration of some antibiotics may also induce side effects in susceptible individuals, for example, by interfering with or modifying metabolic pathways.

As such, there remains a need for development of potent and long-lasting antibiotics that do not induce resistance.

SUMMARY

The disclosure describes techniques and compositions for treating a bacterial infection. In some embodiments, a composition includes a therapeutically effective amount of a histidine kinase inhibitor for treating a bacterial infection. The histidine kinase inhibitor includes at least one of a 6-benzo[d]thiazol-2-amine derivative, a purine derivative, an adenine derivative, an adenine-sulfonyl fluoride derivative, a riluzole analog, a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative.

The details of one or more examples are set forth in the accompanying drawings and the description below. Other features, objects, and advantages will be apparent from the description and drawings, and from the claims.

DETAILED DESCRIPTION

The disclosure describes techniques and compositions for treating bacterial infections. In some embodiments, compositions according to the disclosure include histidine kinase inhibitors.

Agents that inhibit bacterial protein targets, for example, targets that bacteria would find difficult to evade through traditional resistance mechanisms, may act as antivirulence or antibiotic agents, without inducing antibiotic resistance. Histidine kinases may serve as such a bacterial target, and in some embodiments according to the disclosure, compositions including histidine kinase inhibitors may act as one or more of antivirulence or antibiotic agents (collectively, antibacterial agents). The virulence of an organism is the pathogenicity or the propensity for an organism to cause disease, for example, by an infection. An antivirulence agent reduces the virulence of a target organism. An antibiotic is a pharmaceutical agent that inhibits the growth of or kills bacteria. Thus, antibacterial agents in this disclosure refers to agents that reduce the virulence of target organisms, agents that reduce the rate of growth of target bacteria, agents that maintain the rate of growth below a threshold, agents that substantially reduce bacterial populations, or agents that substantially kill a majority of bacteria implicated in an infection. Some antibacterial agents according to the disclosure may also be effective against other organisms, for example, yeasts such as *Schizosaccharomyces pombe* and *Saccharomyces cerevisiae*, fungi, such as *Candida albicans*, and molds, such as *Dictyostelium discoideum*.

Figure 1:
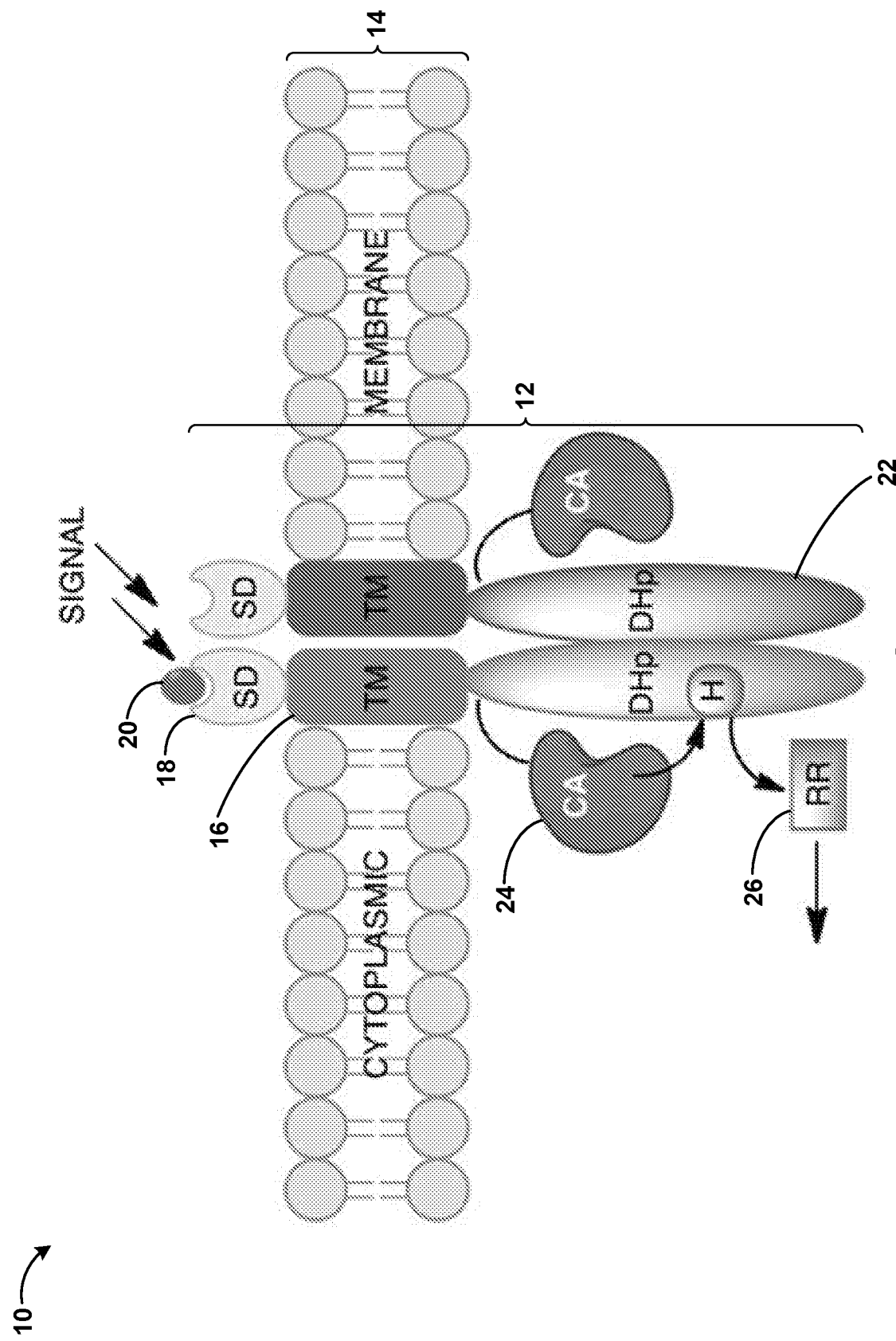
FIG. 1 is a conceptual diagram illustrating a bacterial histidine kinase system.

FIG. 1 is a conceptual and schematic diagram illustrating a bacterial two-component system (TCS) 10. TCS system 10 includes a histidine kinase 12 bound to cytoplasmic membrane 14. For example, cytoplasmic membrane 14 may include a lipid bilayer forming a cell wall of a bacterial organism. Histidine kinase 12 may include a transmembrane domain 16, a sensor domain 18 receptive to an external signaling molecule 20, a dimerization and histidine phototransfer (DHp) region 22, and a catalytic region 24 that binds the natural substrate, adenosine triphosphate (ATP), on receiving a signal. Most bacteria sense and respond to environmental changes through a phosphorylation cascade using TCSs, for example TCS 10, which include histidine kinases(s) 12 (HKs) and their cognate response regulators (RRs) 26, as shown in FIG. 1.

Histidine kinase 12 responds to external stimuli, for example, binding of a signaling molecule 20 to sensor domain 18, which leads to ATP binding in catalytic region 24. The γ-phosphate of the ATP is transferred to a histidine residue in DHp region 22, followed by a transfer of a phosphoryl group to response regulator 26. The activated response regulator 26 causes altered gene expression in bacteria including histidine kinase 12. For example, response regulator 26 may be or include a transcription factor that induces altered gene expression.

TCS 10 may regulate bacterial pathways, for example, cell wall metabolism (YycFG, DesKR), biofilm formation (KinAB), and virulence (PhoPR, WalKR), and may be linked to antibiotic resistance, for example, vancomycin resistance in *Staphylococcus aureus* (VraSR, GraSR), multidrug resistance in *Mycobacterium tuberculosis* (MtrAB), and aminoglycoside resistance in *Acinebactor baumannii* (AdeSR). Many bacteria rely heavily on TCSs (for example, having over 20 distinct TCSs per organism) to respond to their external environment and transmit various cell signals.

While some TCSs or histidine kinases are implicated in the virulence exhibited by multi-drug resistant microbes, they may not be essential for their growth. Without being bound by theory, histidine kinases may therefore serve as therapeutic targets that will be less susceptible to the rapid evolution of resistance. For example, agents that inhibit one or more histidine kinases in bacteria may block signaling pathways and act as antivirulence agents.

TCSs and histidine kinases may be important for bacterial survival, metabolic, and virulence mechanisms. For example, histidine kinases are linked to severe infections caused by both gram-positive and gram-negative bacteria, including *Streptococcus pneumoniae*, resistant *Staphylococcus* and the ESKAPE pathogens (*Enterococcus faecium, S. aureus, Klebsiella pneumoniae, Acinetobacter baumannii, Pseudomonas aeruginosa,* and *Enterobacter* species). Many infectious-agent phenotypes are consequences of TCS signaling, for example, quorum sensing in pneumonia and antibiotic resistance in staph infections. At the molecular level, TCSs affect processes such as chemotaxis, biofilm formation, or secretion system stimulation.

Genetic inactivation of histidine kinase proteins attenuates virulence-associated signaling, and thus, histidine kinase inhibition by small molecules may be therapeutically effective. For example, inhibitors that disarm multiple signal transduction networks in a single cell could cut off all paths of virulence retention or survival by the bacterium. Furthermore, multi-targeted therapy may decelerate drug resistance development, as the mutation of several drug target-encoding genes concurrently is a low-probability event. These factors, along with the fact that histidine kinases are principally found in bacteria or lower eukaryotes and not in humans, indicate that agents that target histidine kinases may be effective antibacterial targets without inducing side effects in humans.

Many histidine kinases exhibit a highly-conserved ATP-binding domain. Thus, targeting the highly conserved ATP-binding domains of histidine kinases may simultaneously deactivate several TCSs in a wide range of bacteria. For example, genetic mutation of single histidine kinase or TCS genes affects signaling and phenotypes at the cellular level. For example, the PhoP/PhoQ two-component system is essential for the virulence of *Salmonella enterica* serovar *Typhimurium* in a murine infection model. In addition to virulence, antibiotic resistance has also been linked to TCSs. For example, the VanSNanR TCS is linked to vancomycin resistance *S. aureus*.

While targeting a particular TCS system may be effective to some extent, disabling several pathways simultaneously, for example, by administering an agent that is an effective inhibitor of multiple TCS systems within one organism or across different organisms may amplify the effects on bacterial virulence and survival, while concomitantly decreasing resistance. For example, a universal histidine kinase inhibitor may provide a global deactivation of bacterial signaling.

In some embodiments, histidine kinase agents according to the disclosure target a histidine kinase ATP-binding domain characterized by a Bergerat fold, a sandwich of a helices in one layer and mixed β strands in another, along with a discrete and flexible ATP lid. Without being bound by theory, the Bergerat fold is not found in other kinases or the small number of mammalian histidine kinases. Thus, the Bergerat fold confers a point of selectively among abundant eukaryotic kinaes. Within the Bergerat fold in the ATP-binding domain, homology boxes (G1-, G2-, G3-, F-, and N-boxes) recognize and participate in specific interactions with the nucleotide. For example, an invariant Asp in the G1-box forms a hydrogen bond with the N6 exocyclic amino group of ATP; the G1-, F-, and G3-boxes position adenosine; and the N-box contains polar residues that coordinate the phosphate groups and chelate a $Mg^{2+}$ ion.

Histidine kinases can be divided into subfamilies. However, a majority of histidine kinases possess all the homology boxes used to describe conservation across the histidine kinase superfamily. HK853 (*Thermotoga maritima*) is a class-1 histidine kinase that can be produced in sufficient quantities for a large screen and is stable and active over extended periods. VicK (*Streptococcus pneumoniae*; homologous to WalK or YycG) is a class-1 histidine kinase and forms an essential TCS in low-GC Gram-positive bacteria. CheA (*Escherichia coli*; class-9) is a chemotactic histidine kinase that exhibits a distinct organization of its domains. While many of CheA's ATP-binding residues are conserved with regard to the histidine kinase superfamily, sufficient variation exists to make CheA unique (e.g., N- and F-boxes). Thus, molecules capable of inhibiting two or three of these proteins, may serve as general scaffolds useful for the development of wide-scale histidine kinase inhibitors in numerous bacterial species.

In some embodiments, a composition according to the disclosure includes a histidine kinase inhibitor for treating a bacterial infection. The histidine kinase inhibitor may include at least one of a 6-benzo[d]thiazol-2-amine derivative, a purine derivative, an adenine derivative, an adenine-sulfonyl fluoride derivative, a riluzole analog, a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative. Purine derivatives according to this disclosure include, for example, adenine derivatives.

A derivative of a scaffold, or an analog of a compound, is a structure formed by replacing one or more components of the scaffold or compound with predetermined functional groups, atoms, or molecules. For example, one or more sites of a scaffold may be substituted with one or more of H, $CH_3$, $OCH_3$, $COCH_3$, Cl, $NO_2$, $CF_3$, $NH_2$, $SO_3H$, $SO_2F$, or another predetermined functional group or atom. The functional group may include one or more of elemental atoms, alkyl groups, alkoxy groups, aryl groups, heteroaryl groups, amines, alcohols, halogens, or derivatives thereof. The substitution may be in one or more positions of the base ring, a core structure, a side group, or a side chain of the scaffold. Thus, the term derivative includes structural analogs.

Figure 2A:
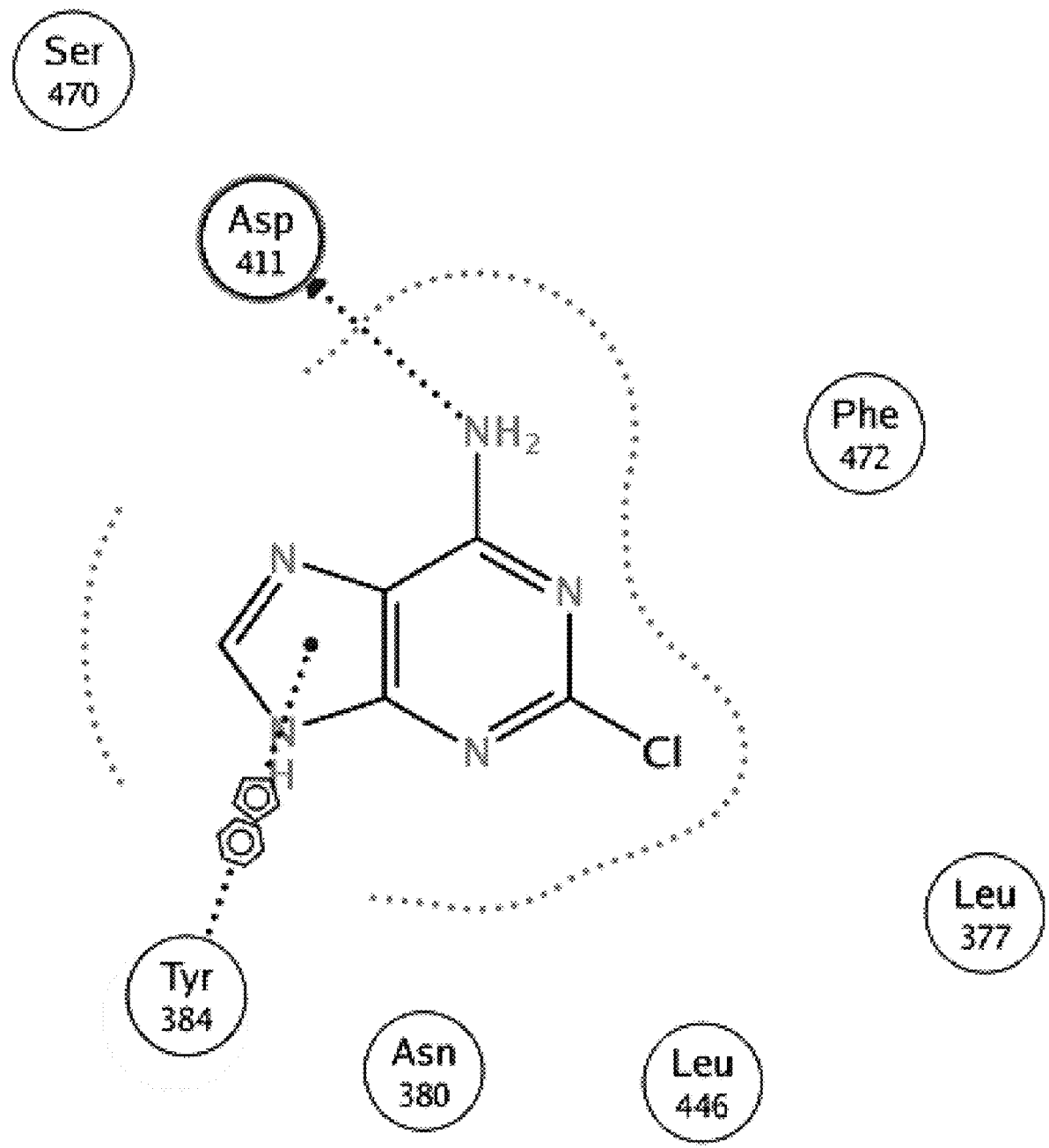
FIG. 2A is a conceptual diagram of modeled interaction between adenine and different sites of histidine kinase HK853.
Figure 2B:
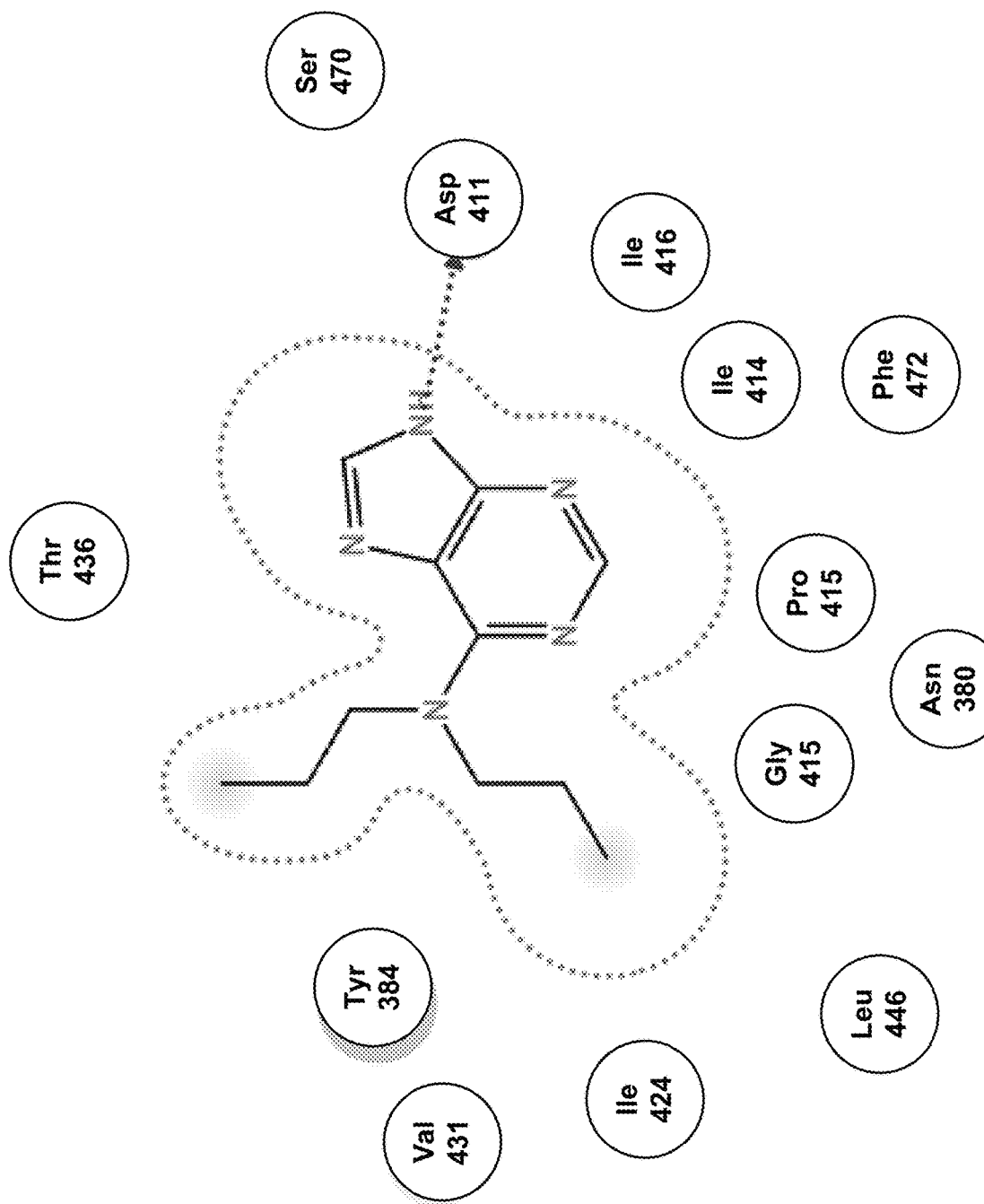
FIG. 2B is a conceptual diagram of modeled interaction between an adenine derivate, n,n-Dipropyladenine, and different sites of histidine kinase HK853.
Figure 2C:
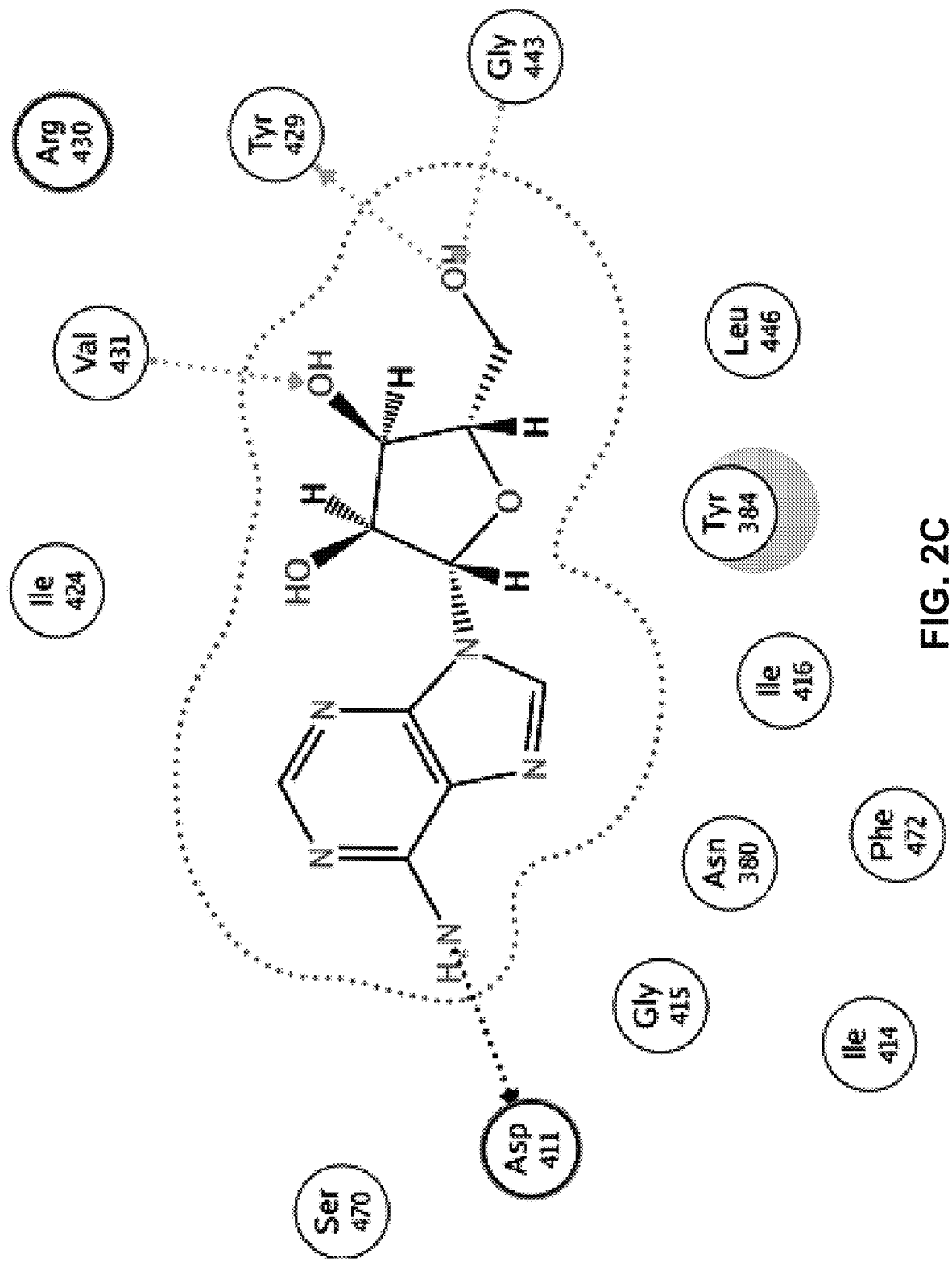
FIG. 2C is a conceptual diagram of modeled interaction between an adenine derivate, adenosine, and different sites of histidine kinase HK853.
Figure 2D:
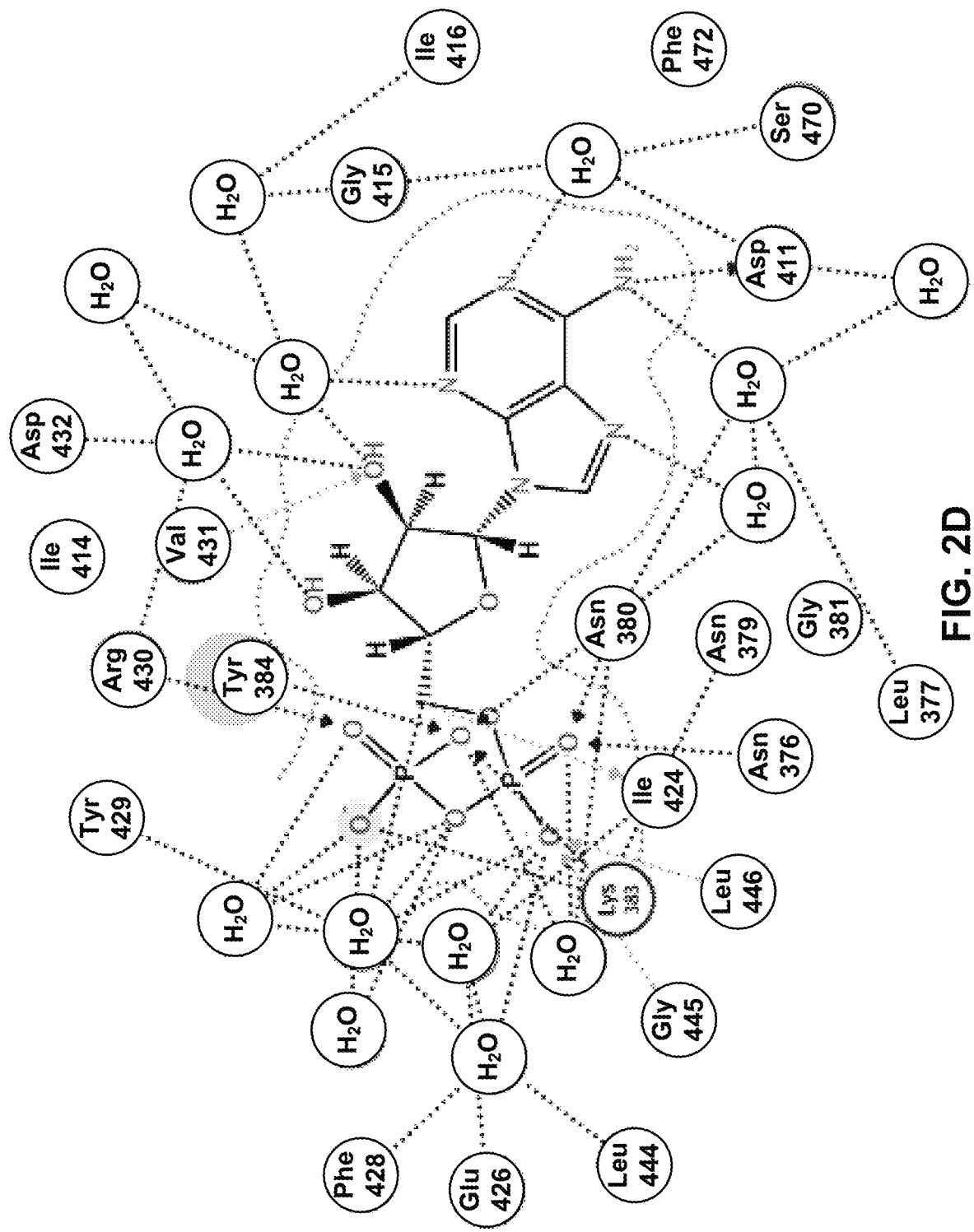
FIG. 2D is a conceptual diagram of modeled interaction between an adenine derivate, adenosine diphosphate (ADP-β-N) and different sites of histidine kinase HK853.

FIG. 2A is a conceptual and schematic diagram of interaction between adenine and different sites of histidine kinase HK853. FIG. 2B is a conceptual and schematic diagram of interaction between an adenine derivate, n,n-Dipropyladenine, and different sites of histidine kinase HK853. FIG. 2C is a conceptual and schematic diagram of interaction between an adenine derivate, adenosine, and different sites of histidine kinase HK853. FIG. 2D is a conceptual and schematic diagram of modeled interaction between an adenine derivate, adenosine diphosphate (ADP-β-N) and different sites of histidine kinase HK853.

The interaction maps shown in FIGS. 2A, 2B, 2C, and 2D were generated using Molecular Operating Environment (MOE) 2013.08 software application (available from Chemical Computing Group ULC, Montreal, Canada). As seen in FIGS. 2A, 2B, and 2C, the inhibitors 2-Chloroadenine, n,n-Dipropyladenine, and adenosine, while having similar chemotypes, exhibited different binding poses with HK853. However, some common features could still be found in these binding poses with HK853, for example the N—NH—N triad present in all of the compounds are in close proximity and potentially interacts with conserved residues like Gly415:Asp411:Asn380, as seen with the ADP-HK853 co-crystal structure interactions in FIG. 2D.

In some embodiments, suitable salts of the derivatives may be used, for example, a salt of one or more derivatives and one or more of cations or anions. The cation may include one or more of aluminum, arginine, benzathine, calcium, chloroprocaine, choline, diethanolamine, ethanolamine, ethylenediamine, histidine, lithium, lysine, magnesium, meglumine, potassium, procaine, sodium, triethylamine, or zinc, or any other suitable cation. The anion may include one or more of acetate, aspartate, benzenesulfonate, benzoate, besylate, bicarbonate, bitartrate, bromide, camsylate, carbonate, chloride, citrate, decanoate, edetate, estolate, esylate, fumarate, gluceptate, gluconate, glutamate, glycolate, glycollylarsanilate, hexanoate, hexylresorcinate, hydrabamine, hydroxynaphthoate, iodide, isethionate, isethionate, lactate, lactobionate, malate, maleate, mandelate, mesylate, methylbromide, methylnitrate, methylsulfate, mucate, napsylate, nitrate, octanoate, oleate, pamoate, pantothenate, phosphate, polygalacturonate, propionate, salicylate, stearate, subacetate, succinate, sulfate, tartrate, teoclate, tosylate, or triethiodide, or any other suitable anion.

In some embodiments, the 6-benzo[d]thiazol-2-amine derivative includes a compound having a structure

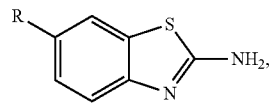

where $R=CH_3$, Cl, $NO_2$, $OCH_3$, or $CF_3$.

In some embodiments, the purine derivative includes a compound having a structure chosen from:

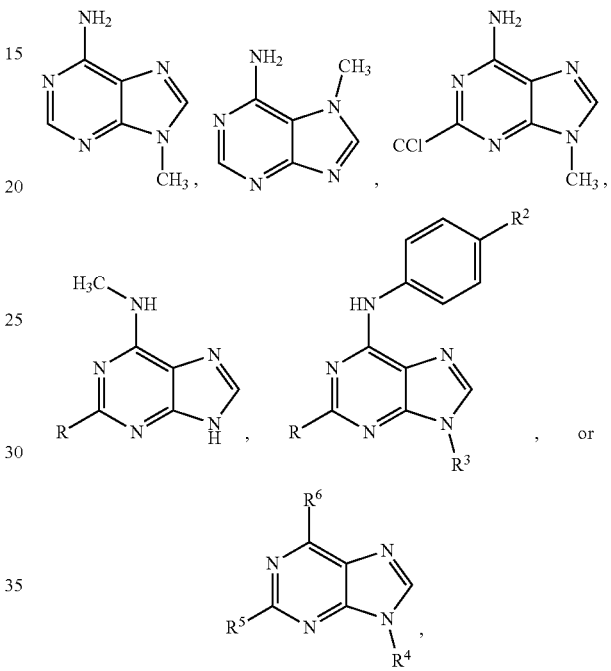

where $R=H$ or Cl, $R^1=H$ or Cl, $R^2=H$, Cl, or F, $R^3=H$ or ribose, $R^4=H$ or ribose, $R^5=H$, $NH_2$, Cl, or F, and $R^6=H$, Cl, or $NH_2$.

In some embodiments, the adenine-sulfonyl fluoride derivative includes a compound having a structure chosen from:

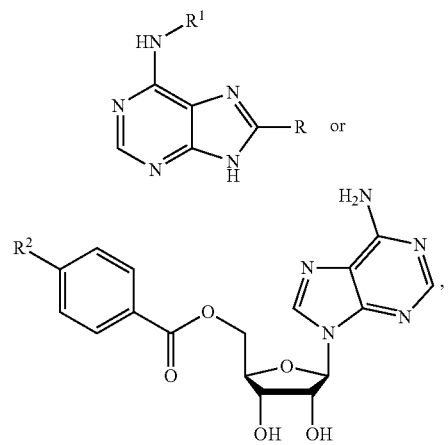

where R=H or

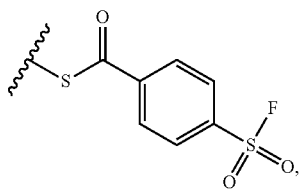 [SMILES: *SC(=O)c1ccc(S(=O)(=O)F)cc1]

$R^1$=H or

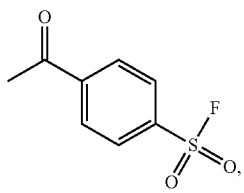

and $R^2$=H, $SO_3H$, or $SO_2F$.

In some examples, the 6,6'-oxybis(benzo[d]thiazol-2-amine) derivative includes a compound having a structure

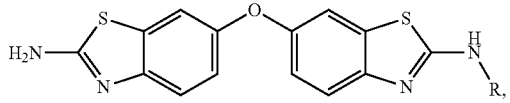

where R=COCH₃ or

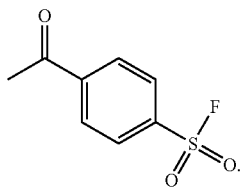

Figure 3:
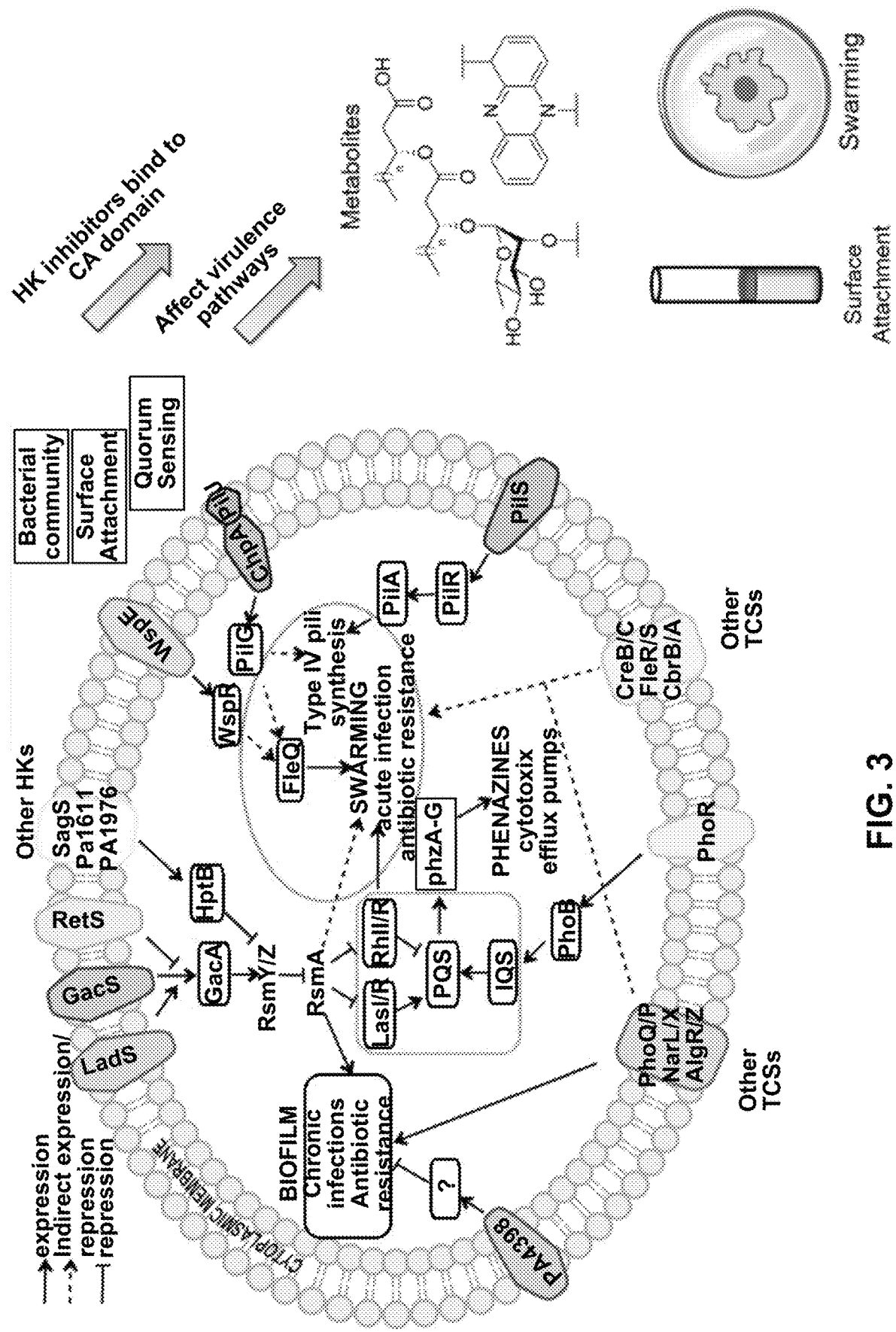
FIG. 3 is a conceptual diagram of virulence pathways in *P. aeruginosa* regulated by various two-component systems (TCSs).

FIG. 3 is a conceptual diagram of virulence pathways in *P. aeruginosa* regulated by various two-component systems (TCSs). Blocking these signaling networks with histidine kinase inhibitors may affect virulence mechanisms. The transmembrane proteins (different indicate assorted HKs and their cognate RRs are shown as grey ovals in the interior. The virulent *P. aeruginosa* strain PA14, obtained from a burn wound, encodes a large number of TCS regulatory proteins in its genome, with >64 sensor HKs and >72 RRs. Not all *P. aeruginosa* strains possess all of the HKs shown in FIG. 3. For example, PA14 does not have LadS, whereas this protein is found in the commonly studied lab strain, PAO1. As shown in FIG. 3, many HKs are intricately linked and influence virulence and antibiotic-resistance mechanisms such as biofilm formation, swarming, and toxin production. Inhibitors of these TCSs or HKs may provide viable leads for treatment of *P. aeruginosa* infection. Riluzole and riluzole analogs may act as histidine kinase inhibitors, for example, HKs associated with *P. aeruginosa*, or with other organisms.

In some examples, a histidine kinase inhibitor includes a riluzole analog. For example, the riluzole analog may include a compound having a structure chosen from:

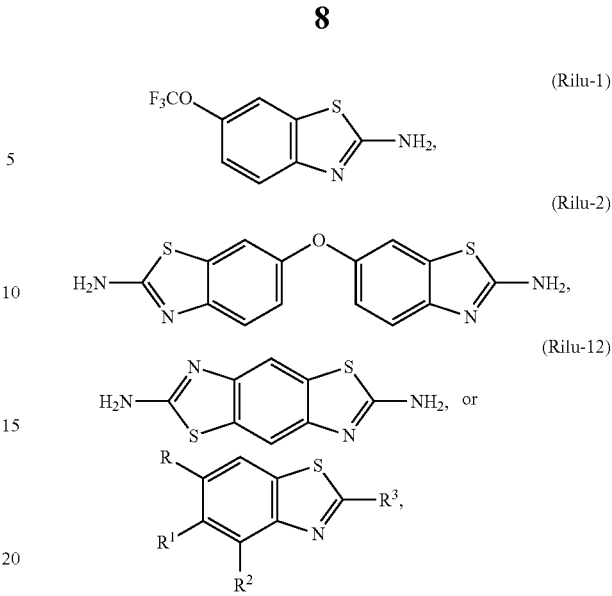

where R=$CH_3$, $R^1$=H, $R^2$=H, $R^3$=$NH_2$ (Rilu-3); or R=$NO_2$, $R^1$=H, $R^2$=H, $R^3$=$NH_2$ (Rilu-4); or R=Cl, $R^1$=H, $R^2$=H, $R^3$=$NH_2$ (Rilu-5); or R=$CF_3$, $R^1$=H, $R^2$=H, $R^3$=$NH_2$ (Rilu-6); or R=$NH_2$, $R^1$=H, $R^2$=H, $R^3$=$CH_3$ (Rilu-7); or R=$OCH_3$, $R^1$=H, $R^2$=H, $R^3$=$NH_2$ (Rilu-8); or R=$NH_2$, $R^1$=H, $R^2$=H, $R^3$=$NH_2$ (Rilu-9); or R=$NHCH_2$-arylsulfonyl fluoride, $R^1$=H, $R^2$=H, $R^3$=$NH_2$; or R=NHC(O)-arylsulfonyl fluoride, $R^1$=H, $R^2$=H, $R^3$=$NH_2$. In some examples, any of R, $R^1$, $R^2$, or $R^3$ may be any of H, $CH_3$, $NH_2$, $NO_2$, $COF_3$, $SO_2F$, Cl, $CF_3$, a riluzole analog, or any other predetermined functional groups, for example, elemental atoms, alkyl, alkoxy, aryl, heteroaryl, amine, alcohol, halogen, or derivatives thereof. In some examples, one or more of R, $R_1$, $R_2$, or $R_3$ may be part of a ring. In some examples, the histidine kinase inhibitor includes one or more of a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative Rilu-1 has a trifluoromethoxy ($OCF_3$) group at the 6-position on the ring, and Rilu-3 to Rilu-11 are based on this core scaffold. Compounds containing an electron-withdrawing group, such as —$OCF_3$, —$NO_2$, —$CF_3$ may have a relatively higher inhibition of HK autophosphorylation (for example, HK853), while compounds including mildly deactivating —Cl group, may have a reduced potency (for example, Rilu-5). Electron-donating groups such as —$OCH_3$, —$NH_2$ or even a weakly donating moiety such as —$CH_3$ may yield ~10-fold decrease in $IC_{50}$ values (for example, Rilu-3, 8, 9). In some examples, functionalization with multiple deactivating groups may yield inactive compounds. Rilu-2, contains two benzothiazole rings, which may promote additional polar interactions within the active site. Rilu-12, which features two amino moieties but in a more rigid tricyclic structure. Rilu-2 and Rilu-12 exhibit relatively high histidine kinase inhibition.

Thus, histidine kinase inhibitors in compositions according to the disclosure may inhibit at least one histidine kinase, for example, a bacterial histidine kinase. The at least one histidine kinase includes at least one of a gram-positive bacterial histidine kinase, or a gram-negative bacterial histidine kinase, such as HK853, VicK, CheA, PhoQ, or WigK. The histidine kinase inhibitor may be an antibiotic or an antibacterial agent. For example, as discussed elsewhere in the disclosure, the histidine kinase inhibitor may inhibit the growth of bacteria, or may reduce bacterial populations, or substantially result in the death of bacterial populations implicated in a bacterial infection.

Antibacterial agents according to the disclosure may be effective against gram-positive bacteria and gram-negative bacteria, for example, Salmonella, Streptococcus, E. coli, Vibrio cholerae, Pseudomonas aeruginosa, Staphylococcus aureus, Acinetobacter baumannii, Enterobacteriaceae, Clostridium difficile or other bacteria.

In some embodiments, a composition according to the disclosure may include a pharmaceutically effective amount of the histidine kinase inhibitor. The pharmaceutically effective amount may be any suitable amount effective to treat a bacterial infection in a patient. For example, the pharmaceutically effective amount may depend on the bacteria implicated in the infection, the severity of the infection, and the health of the patient. In some embodiments, the pharmaceutically effective amount may include 0.01%, 0.1%, 1%, 2%, 5%, or 10% (weight/weight) of the histidine kinase inhibitor in the composition.

In some embodiments, the composition may include a pharmaceutically acceptable carrier. For example, the pharmaceutically acceptable carrier may include one or more of a cream, a lotion, a spray, a gel, an ointment, a paste, a solution, a suspension, an emulsion, a powder, a liquid, or a solid. In some embodiments, a formulation may include a composition according to the disclosure, and the formulation may be a topical, injectable, parenteral, or oral formulation.

Compositions or formulations according to the disclosure may be used to treat bacterial infections. In some embodiments, a technique may include administering a composition including a histidine kinase inhibitor according to the disclosure to a patient suffering from bacterial infection. The histidine kinase inhibitor may include at least one of a 6-benzo[d]thiazol-2-amine derivative, a purine derivative, an adenine derivative, an adenine-sulfonyl fluoride derivative, a riluzole analog, a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative. In some embodiments, the administering may include topical application, oral consumption, or parenteral injection of a formulation or composition according to the disclosure. In some embodiments, the concentration or amount of histidine kinase inhibitor administered to the patient may be varied depend on the extent and severity of the infection and the health of the patient. For example, administering the composition may include administering a suitable amount, for example, at least 0.1 mg/day, 1 mg/day, 5 mg/day, 10 mg/day, 20 mg/day, 50 mg/day, or 100 mg/day of the histidine kinase inhibitor. The administering may include administering a single dose, or administering multiple doses at predetermined intervals. The dosage may be increased or reduced across different doses in response to changes in the bacterial infection or patient health. In some embodiments, a second antibacterial agent that is not a histidine kinase inhibitor may be administered with the histidine kinase inhibitor. For example, the second antibacterial agent may include a co-antibiotic administered simultaneously or sequentially with the histidine kinase inhibitor. In some examples, the co-antibiotic may include one or more of penicillins, cephalosporins, carbapenems, vancomycin, aminoglycosides, polymyxins, and other known antibacterial agents.

Thus, compositions including histidine kinase inhibitors according to the disclosure may be used to treat bacterial infections.

The present disclosure will be illustrated by the following non-limiting examples.

EXAMPLES

Example 1

A high-throughout screen (~50,000 small molecules, MN≤400 Da) was conducted using a fluorescence polarization (FP) assay to evaluate the binding of target histidine kinase (HK853) by candidate compounds. A fluorescent, nonhydrolyzable adenosine diphosphate (ADP) probe, ADP-BODIPY, having the following structure was used:

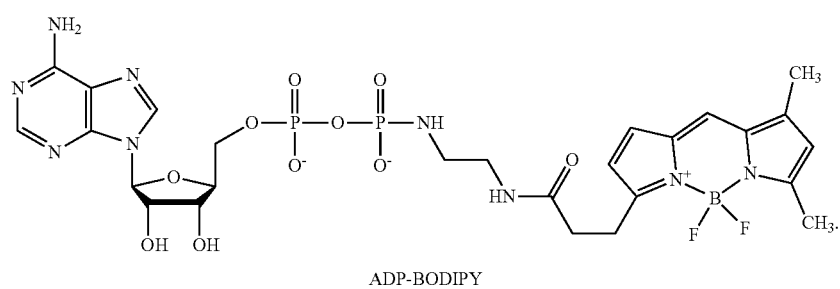

ADP-BODIPY

Once a candidate was found to be active from the screen, its dose dependence inhibitory activity was analyzed using an activity-based probe BODIPY-FL-ATPγS (B-ATPγS). In reaction buffer, 0.46 μM HK853 was preincubated with test compounds (dissolved in DMSO) in 24 μL for 30 min. The addition of 1 μL B-ATPγS brought the final 25-μL reactions to 0.44 μM HK853 and 2 μM B-ATPγS in the presence of competitors and 5% DMSO. Triton X-100 was premixed with reaction buffer to yield 0.1% (v/v) in final 25-μL reactions. Samples were mixed and incubated in the dark at RT for 1 h before quenching with 8.6 μL 2×SDS-PAGE sample loading buffer and loading 10 μL on a 10%0/stacking gel. After SDS-PAGE, in-gel fluorescence detection elucidated HK853 activity, and silver staining of the gels ensured even protein loading. Integrated density values of the fluorescent gel bands were normalized as "% Activity" with respect to a control that contained no inhibitor. Data were plotted in GraphPad Prism (available from GraphPad Software, San Diego, Calif.) with relation to the log of molar inhibitor to determine $IC_{50}$ values, using EQUATION 1.

$$y = \text{Bottom} + \frac{(\text{Top} - \text{Bottom})}{1 + 10^{((\log IC_{50} - x) * \text{HillSlope})}}. \quad \text{(Equation 1)}$$

In EQUATION 1, y is the response, Bottom and Top are plateaus in the units of the y-axis, x is the log of the molar concentration of inhibitor, HillSlope is the slope of the curve, and $IC_{50}$ is the concentration of compound required for 50% inhibition (a response halfway between Bottom and Top).

The $IC_{50}$ was established for different adenine derivatives. The results are shown in TABLE 1. A lower $IC_{50}$ is indicative of better affinity/inhibition. In TABLE 1, "N/I" indicates that no inhibition was observed. The structure of the scaffold of the adenine structure that was substituted to prepare the compounds of TABLE 1 is:

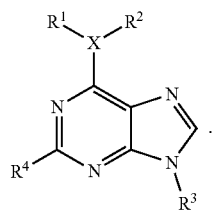

TABLE 1

| Candidate Compound No. | X | R¹ | R² | R³ | R⁴ | $IC_{50}$ (μm) |
|---|---|---|---|---|---|---|
| C12 | N | H | H | ribose | H | 445 |
| C13 | N | H | H | CH₃ | H | 145 |
| C14 | Cl | — | — | — | H | 235 |
| C15 | N | C₆H₅ | H | H | H | 7.6 |
| C18 | Cl | H | H | ribose | H | N/I |
| C19 | N | n-C₃H₈ | n-C₃H₈ | ribose | H | 1100 |
| C20 | N | C₂H₄C₆H₅ | H | ribose | H | 1200 |
| C21 | N | C₂H₄C₆H₅ | H | ribose-2PO₄ | H | 1200 |
| C24 | N | H | H | H | NH₂ | N/I |
| C26 | N | H | H | 7-CH₃ | H | N/I |
| C27 | O | — | — | ribose | NH₂ | N/I |

As seen in TABLE 1, addition of ribose to compounds C12, and C18-C21 did not appear to improve their affinity (inhibition of HK853). The presence of either 6-NH2 or 9-NH may improve inhibition, as removing them in compounds C18 and C27 appeared to diminish affinity. The functionalization on C-2 position of adenine affected inhibition. For example, an amino group at C-2 appeared to reduce affinity in compound C24. Providing a phenyl ring at 6-NH2 appeared to improve the affinity of compound C15. Thus, providing a cyclic or hydrophobic group at C-6 improves the affinity. Thus, the affinity (or inhibition) of HK853 by different compounds was evaluated. Providing a CH₃ at N-7 appears to diminish affinity, while providing a CH₃ at N-9 improves affinity (inhibition).

Example 2

The inhibition of histidine kinase HK853 by candidate purine derivatives was evaluated. The purine scaffold had the following structure:

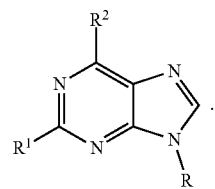

The inhibition of histidine kinase HK853 by candidate purine derivatives is summarized in TABLE 2. The functionalization on C-2 position of purine affected inhibition. For example, a chloro group at C-2 increased affinity of compounds CW22 and CW23 by about 3-fold, while an amino group at C-2 appeared to reduce affinity in compound CW28.

TABLE 2

| Candidate Compound No. | Substituents | | | $IC_{50}$ (μm) |
|---|---|---|---|---|
| | R | R¹ | R² | |
| CW18 | H | H | Cl | 1100 |
| CW19 | Ribose | H | Cl | N/I |
| CW20 | H | NH₂ | Cl | 118 |
| CW21 | Ribose | NH₂ | Cl | 1800 |
| CW22 | H | Cl | NH₂ | 156 |
| CW23 | Ribose | Cl | NH₂ | 125 |
| CW24 | H | F | NH₂ | 310 |
| CW25 | Ribose | F | NH₂ | 218 |
| CW26 | H | Cl | Cl | >1250 |
| CW27 | NH₂ | NH₂ | NH₂ | 2100 |
| CW28 | ribose | NH₂ | NH₂ | 21000 |
| CW29 | CH₃ | H | NH₂ | 150 |
| CW30 | 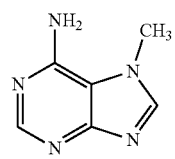 | | | N/I |
| CW31 | CH₃ | Cl | NH₂ | 93 |
| CW32 | H | H | —NH—CH₃ | 950 |
| CW33 | H | Cl | —NH—CH₃ | 830 |

Example 3

The inhibition of histidine kinase HK853 by candidate phenyl-adenine derivatives was evaluated. The phenyl-adenine scaffold had the following structure:

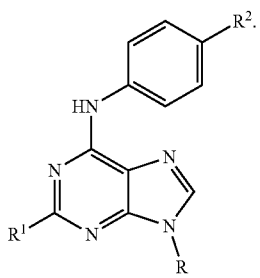

The inhibition of histidine kinase HK853 by candidate purine derivatives is summarized in TABLE 3.

TABLE 3

| Candidate Compound No. | Substituents | | | IC$_{50}$ (μm) |
|---|---|---|---|---|
| | R | R$^1$ | R$^2$ | |
| CW34 | H | H | H | 7.6 |
| CW35 | Ribose | H | H | N/I |
| CW36 | H | Cl | H | N/I |
| CW37 | H | H | Cl | 1700 |
| CW38 | H | H | F | 1900 |

Example 4

The effect of providing sulfonyl fluoride side chains on histidine kinase HK853 inhibition was evaluated. Substituting a hydrogen of 6-O-benzoyl adenosine (at site R in the adenosine scaffold shown below) with SO$_2$F improved inhibition (IC$_{50}$=5.3 μM) compared to that of 6-O-benzoyl adenosine (IC$_{50}$=192 μM). Substituting the same hydrogen with SO$_2$H did not improve inhibition (IC$_{50}$=188 μM). The adenosine scaffold used had the following structure:

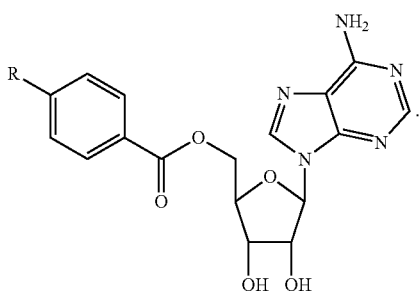

Substituting a hydrogen of a riluzole analog with benzyl SO$_2$F improved inhibition (IC$_{50}$=2.1 μM) compared to that of Rilu-9 (IC$_{50}$=161 μM). The riluzole scaffold used had the following structure:

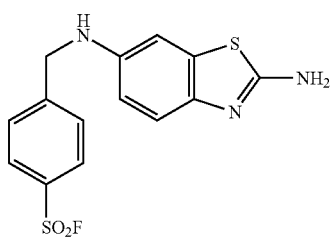 [SMILES: Nc1nc2ccc(NCc3ccc(S(=O)(=O)F)cc3)cc2s1]

Thus, providing a sulfonyl fluoride side chain improved histidine kinase inhibition.

Example 5

The inhibition of PhoQ by histidine kinase inhibitors was evaluated. Salmonella virulence involves TCS-mediated sensing of host innate immune defenses found in the lumen of the small intestine and in macrophage phagosomes. The Salmonella PhoQ protein senses low Mg$^{2+}$, cationic antimicrobial peptides, and acidic pH, leading to PhoP-dependent activation of transcription of genes involved in Salmonella virulence. Because PhoP and PhoQ are required for Salmonella growth in low (10 μM) Mg2$^+$, but are not required for growth in high (10 mM) Mg$^{2+}$, compounds that inhibit PhoQ may prevent Salmonella growth in low Mg$^{2+}$. Using an assay for inhibition of PhoQ, compounds that inhibited wild-type Salmonella growth in media containing low Mg$^{2+}$ were identified. 6,6'-oxybis(benzo[d]thiazol-2-amine) (compound CW7) exhibited OD600 (optical density at 600 nm, indicative of size of Salmonella population) values at a concentration of 250 μM of less than ~0.01 through 6 hours. A purine derivative with the structure

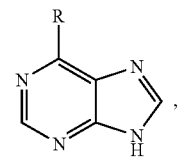

where

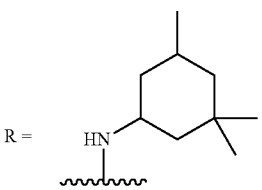 [SMILES: *NC1CC(C)CC(C)(C)C1]

(compound CW14) exhibited OD600 values at a concentration of 250 μM of less than 0.03 through 6 hours. A 6-benzo[d]thiazol-2-amine derivative with the structure

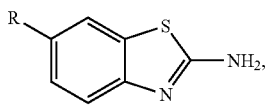

where R=CF$_3$ (compound CW6) exhibited OD600 values at a concentration of 250 μM of less than 0.1 through 6 hours. In comparison, OD600 values for DMSO-treated wild-type culture typically reach ~0.300 by 6 hours. These results indicate that histidine kinase inhibitors may prevent Salmonella from adapting to low Mg$^{2+}$, and that compounds including an aminobenzothiazole scaffold may be effective as PhoQ inhibitors.

Because inhibition of PhoQ is expected to cause a decrease in expression of PhoP target genes, quantitative real-time PCR was used to test whether candidate compounds cause a decrease in mRNA levels of the PhoP target genes phoP and pmrD. The level of 16s rRNA was used to normalize mRNA levels for cell density. Treatment with 62.5 μM of compound CW7 caused a 3.4-fold decrease in phoP mRNA and a 2.2-fold decrease in pmrD mRNA; treatment with 32.5 μM compound 7 caused a 1.8-fold decrease in phoP mRNA and a 1.5-fold decrease in pmrD mRNA, indicating dose-dependence. Treatment with 125 μM of riluzole caused a 2.6-fold decrease in phoP mRNA and a 2-fold decrease in pmrD mRNA. Neither compound affected mRNA levels of plsB, a gene not regulated by PhoP. These results indicate that candidate compounds inhibit PhoQ/PhoP signaling in a wild-type, virulent strain of *Salmonella*.

Example 6

The inhibition of histidine kinase WigK (*Vibrio cholerae*) was evaluated. WigK may provide resistance to beta-lactam antibiotics. WigK may sense antibiotic-induced cell wall damage and in response upregulates the entire cell wall synthesis pathway, and its presence may be crucial for *Vibrio cholerae*'s survival in the presence of beta lactam antibiotics and other inhibitors of cell wall synthesis. Candidate compounds were tested for inhibition of *Vibrio cholerae* and *Vibrio parahaemolyticus* for potentiation of beta lactam antibiotics. Compounds CW7, CW14, and an additional candidate, a purine derivative with the structure

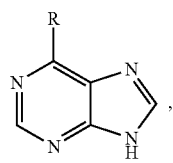

where

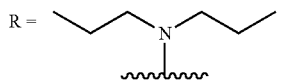 [SMILES: *N(CCC)CCC]

(compound CW11) were found to inhibit *Vibrio cholerae*. Compound CW14, induced lysis in *V. cholerae* during simultaneous treatment with penicillin. 6-benzo[d]thiazol-2-amine derivatives with the structure

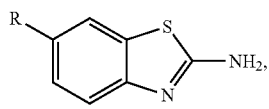

where R=$CH_3$ (compound CW2), Cl (compound CW3), $NO_2$ (compound CW4), $CF_3$ (compound CW6) and compound CW7 had direct killing activity at concentrations of 500 μM. Compound CW7 had potential in *Vibrio parahaemolyticus* because the compound matches the histidine kinase knockout for beta lactam potentiation.

Example 7

The inhibition of pathogenicity of *P. aeruginosa* by riluzole analogs was evaluated by assessing production of two major classes of molecules involved in signaling and infection establishment, the *Pseudomonas* quinolone signals (PQSs) and the phenazines. At the TCS level, pathways such as GacS/GacA-RetS and PhoR/PhoB are associated with the formation of PQSs and phenazine metabolites via the QS system and small RNAs machinery.

Figure 4:
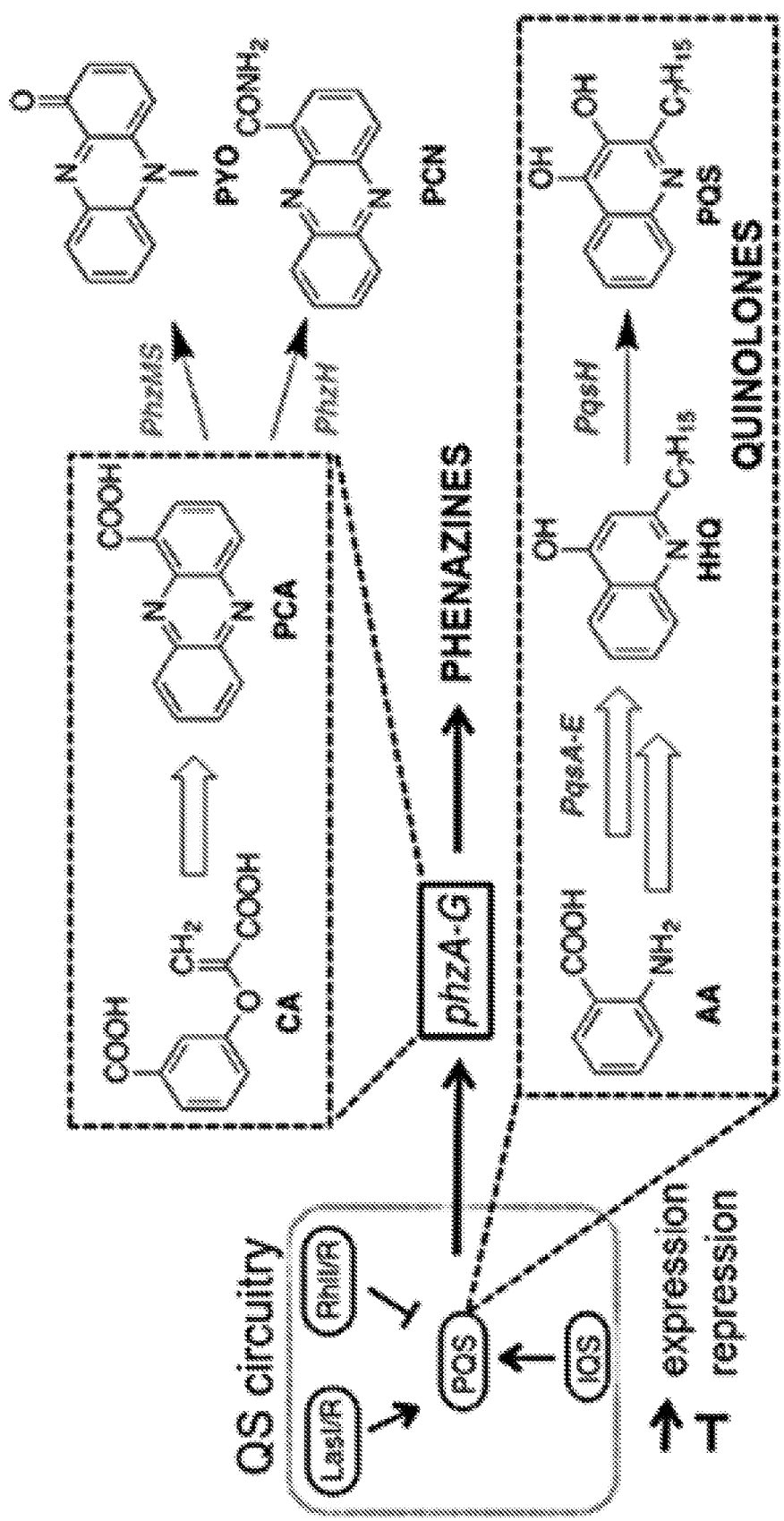
FIG. 4 is a conceptual diagram showing a model of biosynthetic pathways for production of virulence-related metabolites and their relation to the quorum sensing (QS) network.

FIG. 4 is a conceptual diagram showing a model of biosynthetic pathways for production of virulence-related metabolites and their relation to the quorum sensing (QS) network. As illustrated in FIG. 4, production of the QS signals is tightly regulated by several circuits. The PQS system autoregulates the production of quinolone-type compounds, which have roles in controlling other toxins and virulence behaviour in *Pseudomonas*. When a quorum is reached, biosynthesis of 4-hydroxy-2-heptylquinoline (HHQ) and 3,4-dihydroxy-2-heptylquinoline (PQS) is initiated by the production of their precursor, anthranilic acid (AA). The release of PQS then activates the phenazine-producing genes phzA-G that convert chorismic acid (CA) to the primary phenazine metabolite, phenazine-1-carboxylic acid (PCA). From different cues, PCA can be modified to phenazine-1-carboxamide (PCN) and to the other crucial toxin of *P. aeruginosa*, pyocyanin (PYO). The expulsion of these toxic metabolites (quinolones, phenazines) is regulated by TCSs and as such, inhibiting the production of these toxins may constitute a viable antibacterial therapy.

The influence of riluzole analogs on these metabolites was measured by LC-MS analyses on supernatant of PA14 cultures grown in the presence or absence of inhibitors at various growth phases.

Figure 5A:
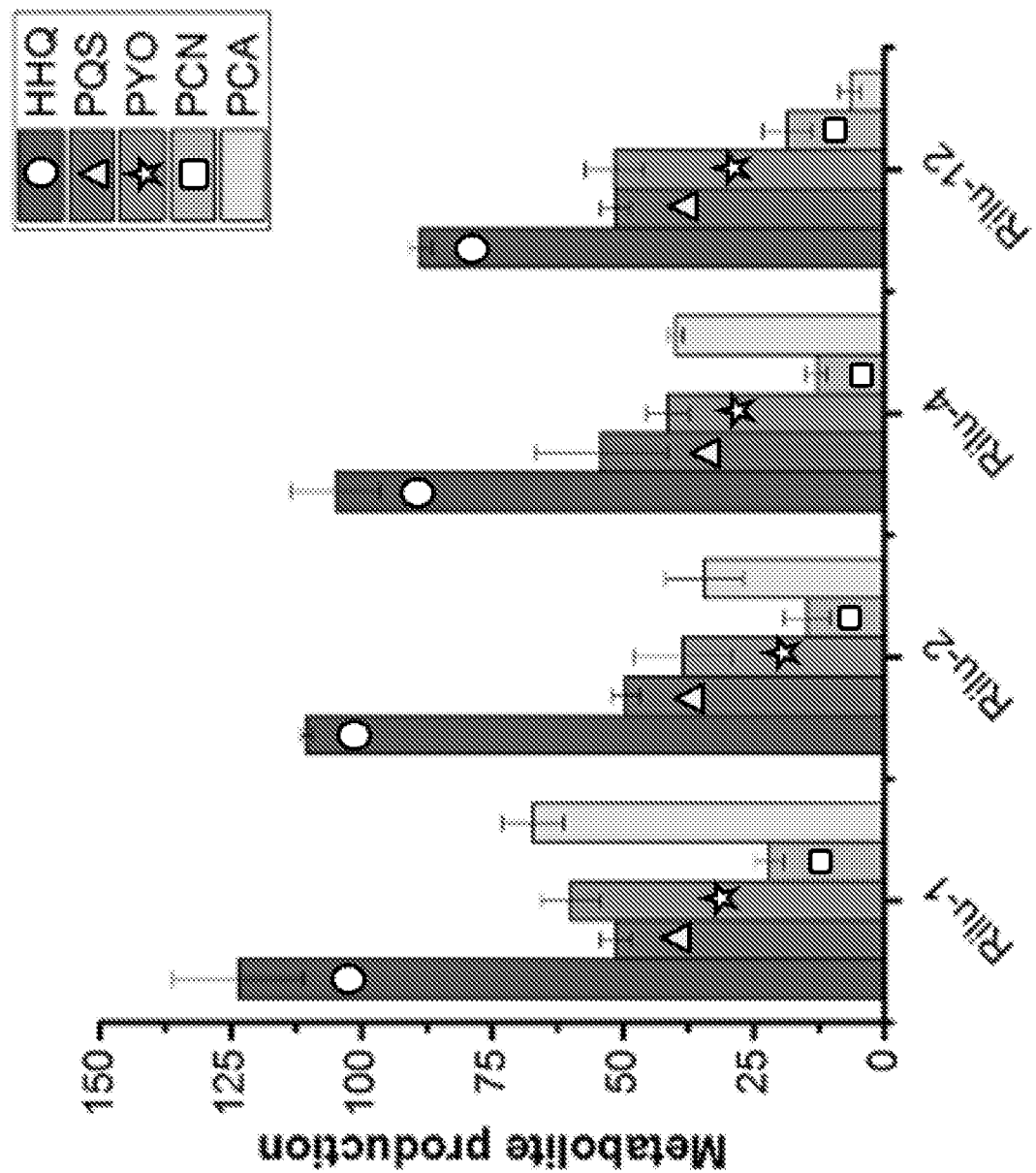
FIG. 5A is a graph showing effect of riluzole analogs on the production of metabolites in *P. aeruginosa* strain PA14 at 200 μm after 9 hours of incubation at 37° C. and 200 RPM.
Figure 5B:
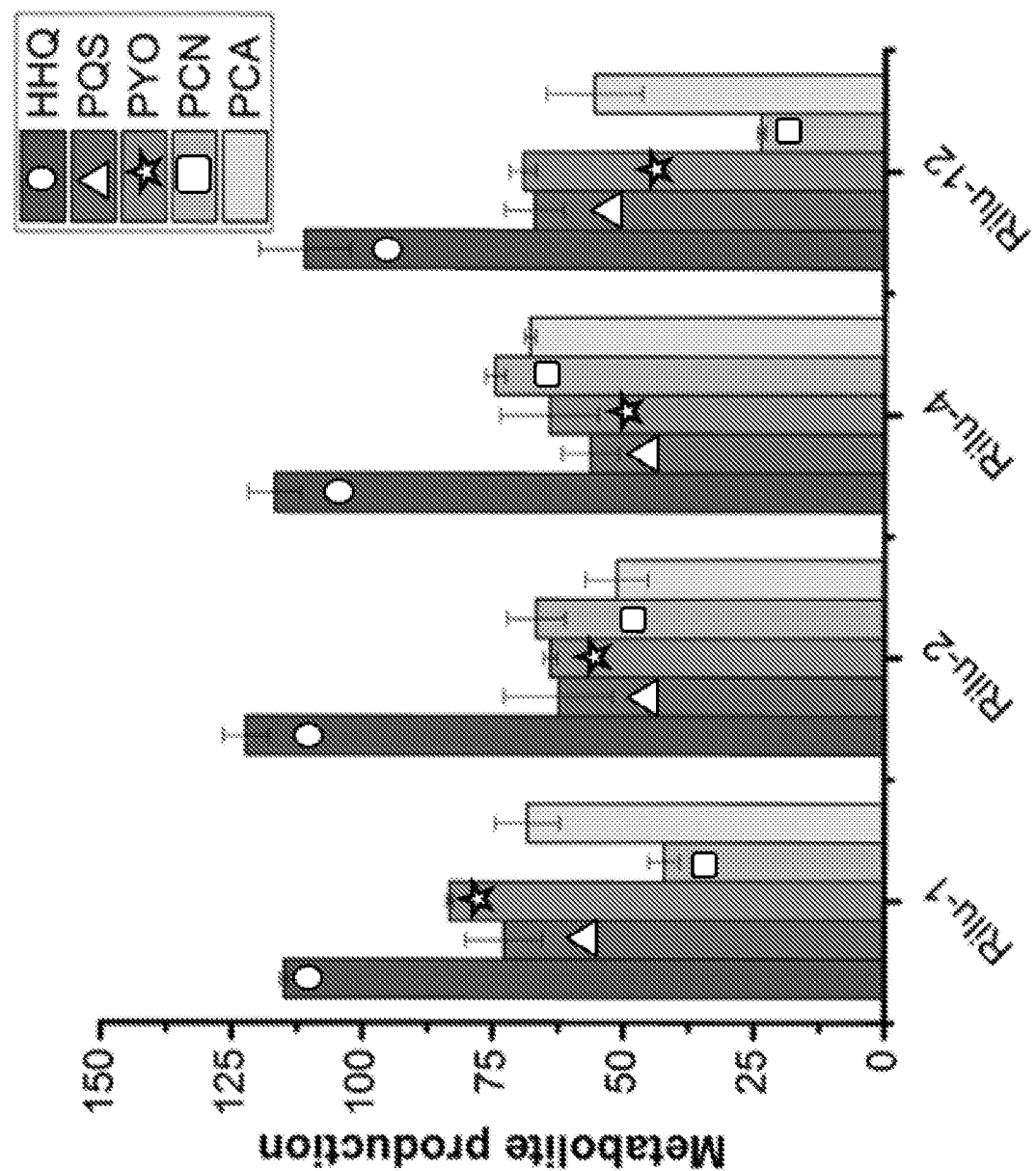
FIG. 5B is a graph showing effect of riluzole analogs on the production of metabolites in *P. aeruginosa* strain PA14 at 200 μm after 24 hours of incubation at 37° C. and 200 RPM.

FIG. 5A is a graph showing effect of riluzole analogs on the production of metabolites in *P. aeruginosa* strain PA14 at 200 μm after 9 hours of incubation at 37° C. and 200 RPM. FIG. 5B is a graph showing effect of riluzole analogs on the production of metabolites in *P. aeruginosa* strain PA14 at 200 μm after 24 hours of incubation at 37° C. and 200 RPM. All values are plotted relative to a DMSO-treated control and normalized to the final cell density ($OD_{620}$). The $OD_{620}$=0.9 in FIG. 5A, $OD_{620}$=1.8 in FIG. 5B. Error bars represent the standard error of two independent experiments (b) PA14 cultures after 24 hours ($OD_{620}$~1.8) in presence of riluzole analogs and DMSO at 500 μM. As seen in FIG. 5A, although the levels of HHQ were slightly increased upon treatment (Rilu-1, ~24%), PQS production was markedly decreased (~50%) by all inhibitors compared to the DMSO control. Null mutation of the pqs system may affect other virulence factors such as PYO, elastase, and rhamnolipids (RLs). In addition, up to a 70% reduction of PYO was achieved (Rilu-2), while PCN was reduced by ~85% (Rilu-2) and finally, only negligible amounts of PCA (~8%) were produced with Rilu-12.

Visual inspection of *P. aeruginosa* cultures was used to corroborate these results. A significant reduction in the characteristic blue-green hue of *P. aeruginosa* cultures, which is due to the phenazines, was observed after a 24 hour treatment with inhibitors Rilu-1, Rilu-2, Rilu-4, and Rilu-12. These cultures were observed to exhibit turbidity, indicating that bacterial growth was not impeded by the compounds, and that the striking reductions in toxin production were likely caused by interfering with TCS machinery component(s).

Example 8

The inhibition of virulence of *P. aeruginosa* by riluzole analogs was evaluated. Microorganisms may rely on biofilm formation to establish a cellular community. In *P. aeruginosa*, biofilm formation is controlled by a complex web of many TCSs. For example, TCSs GacS/GacA, PhoQ/PhoP, and NarL/NarX positively regulate biofilm formation, but when sensor kinase PA4398 was mutated in a P. aeruginosa isolate, PA14, a 1.8 fold increase in biofilm production was observed. Using a microtitre assay, ~40% reduction of biofilm formation of PA14 cultures was observed using compounds Rilu-2 and Rilu-4, at relatively high concentrations. Examination of these microbial biofilms can provide insights into a microorganism's ability to attach to solid surfaces, as alterations in appendages like flagella and type IV pili may result in significant architectural changes. Accordingly, the initial surface adhesion of microorganism that is dependent on flagella/pili formation, was assessed with a rapid attachment assay.

Figure 6:
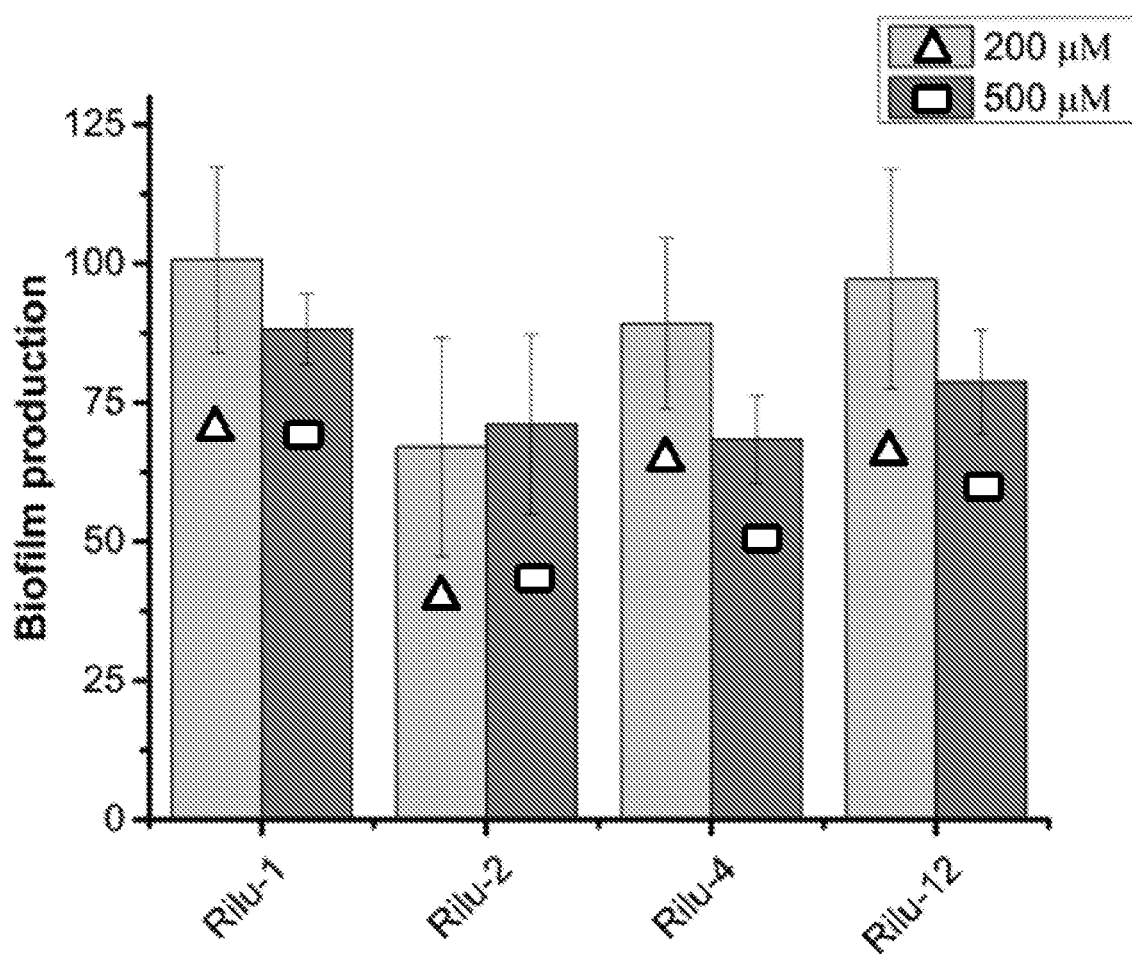
FIG. 6 is a graph showing the results of attachment assay for *P. aeruginosa* strain PA14 in the presence of riluzole analogs.

FIG. 6 is a graph showing the results of attachment assay for P. aeruginosa strain PA14 in the presence of riluzole analogs. P. aeruginosa PA14 strain was grown overnight (~16 h) in LB media at 37° C. and 200 RPM. The overnight cultures were washed and diluted in LB medium to an $OD_{620}$ value of 1.0. 100 µL of this suspension was used to inoculate each well of a microtiter plate in presence of riluzole analogs in DMSO at 200 µM or 500 µM (for the control experiments, same amount of DMSO was added). 8 wells per plate were used for each sample. Cells were allowed to adhere for 60 min at 37° C. and 200 RPM. After the planktonic cells were removed, staining with crystal violet was carried out, as described in the biofilm assay procedure. Assays were repeated in triplicate. All values are plotted relative to a DMSO-treated control and normalized to the final cell density ($OD_{620}$). As seen in FIG. 6, notable differences in surface attachment was observed with the different Rilu-compounds Rilu-1, Rilu-2, Rilu-4 and Rilu-12. In particular, a 70% reduction occurred in cultures containing Rilu-4 and Rilu-12.

Example 9

The inhibition of swarming or motility of P. aeruginosa by riluzole analogs was evaluated. Activation of HKs, such as chemotaxis-related WspE, ChpA and the nitrogen acquisition-related, PilS, have been linked to flagella and pili-synthesis. The significant effect of Rilu-compounds in the attachment assay of EXAMPLE 8 indicated that Rilu-compounds may affect the motility of P. aeruginosa. Pseudomonas is unique in its application of versatile motility modes and among these, swarming may enable the deadly pathogen to move through mucosal layers in CF patients based on nutritional and viscosity variations. The coordinated movement of bacteria using both flagella and type IV pili may exhibit a greater resistance to multiple antibiotics and express higher levels of virulence-related factors compared to planktonic cultures. Swarming is TCS-dependent, as HKs gacS, fleS and the alginate RR algR mutants are all impaired in swarming motility.

Plates consisted of modified M9 medium [20 mM $NH_4Cl$; 12 mM $Na_2HPO_4$; 22 mM $KH_2PO_4$; 8.6 mM NaCl; 1 mM $MgSO_4$; 1 mM $CaCl_2$).$2H_2O$; 11 mM dextrose; 0.5% casa-mino acids (Difco)] solidified with Bacto-agar (Difco). The M9 media without $MgSO_4$ and $CaCl_2.2H_2O$ was autoclaved, which were added after cooling the media ~60° C. The pH was adjusted after autoclaving with HCl and NaOH (pH=7.5). Then, the plates included a 1-in-100 dilution of filter-sterile stock containing 1 mg/mL Nile red (Sigma Aldrich) dissolved in 85% ethylene glycol (prepared the day of use to limit photoinactivation).[6] 20 mL of this media was poured into Petri dishes, along with the riluzole analogs in DMSO at final concentrations, 125 µM or 200 µM (for the control experiments, same amount of DMSO was added). These were then allowed to dry for 60 min, with the first 20 min under UV light to ensure plates were sterile following pH adjustment. P. aeruginosa PA14 strain was grown overnight (~16 h) in LB media at 37° C. and 200 RPM. Five µl of bacteria were then spotted at the center of each plate, which were then incubated at 30° C. in the dark and ~20% humidity. The plates were intermittently taken out for fluorescence scanning [scan settings: GE Typhoon Variable Mode Imager 9500, using 532-nm laser with DY-520XL ($\lambda$ex: 520 nm, $\lambda$em: 664 nm)]. The scans were then visualized and integrated density measurements of whole-plate fluorescence were performed using ImageJ software (U. S. National Institutes of Health, Bethesda, Md., USA). Images of these plates were also taken with a Nikon D5200 DSLR camera, which were then processed in Adobe Photoshop Lightroom 5 (Mac version) for phase-contrast.

Figure 7:
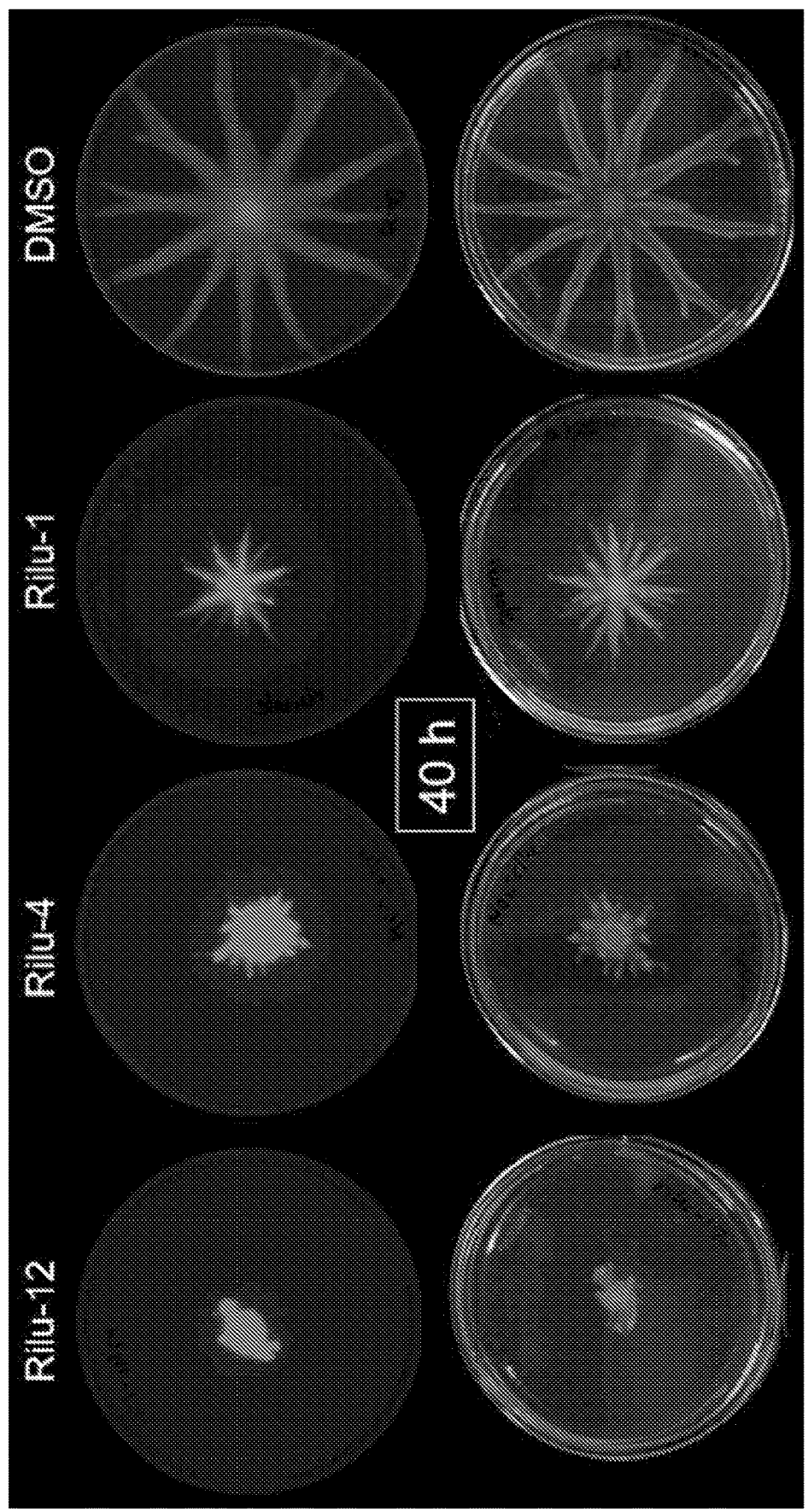
FIG. 7 is a photograph illustrating fluorescence scans (top row) and optical images (bottom row) of microbial plates incubated with *P. aeruginosa* strain PA14 for 40 hours.

FIG. 7 is a photograph illustrating fluorescence scans (top row) and optical images (bottom row) of microbial plates incubated with P. aeruginosa strain PA14 for 40 hours. As seen in the bottom row of FIG. 7, Rilu-compounds (at 200 µM) significantly affected swarming growth. After 40 hours, a marked reduction in tendril formation was observed with all compounds, most prominently with Rilu-12. After 5 days, a moderate difference in swarming was observed with Rilu-1 and Rilu-4, and a significant impairment in motility was observed with Rilu-12. A similar reduction in swarming was also observed with 125 µM of Rilu-4 and Rilu-12, indicating the efficacy of the compounds at lower concentrations.

To reduce surface tension and swarm adequately, P. aeruginosa cells secrete RLs, amphiphilic glycolipids. A fluorescent lipophilic stain, Nile red, that can bind to these glycolipids, was used to visualize the swarming growth of PA14. Similar to the phase-contrast images, the stain is concentrated at the center of the swarm colony for all of the samples at 40 hours, as seen in the top row of FIG. 7. After 5 days, the RLs were evenly distributed throughout the swarm area. The RL levels were quantified at 16 hours, 24 hours, 40 hours and 5 days.

P. aeruginosa PA14 strain was grown overnight (~16 h) in LB media at 37° C. and 200 RPM. This culture was diluted 1:100 into fresh Minimal Medium (49.3 mM $Na_2HPO_4$, 50 mM $KH_2PO_4$, 4.8 mM $MgSO_4$, 7.6 mM $(NH_4)_2SO_4$, 0.6 mM $CaCl_2$, 25 µM $FeSO_4$, 0.162 µM $(NH_4)_6Mo_7O_{24}$, 38 µM $ZnSO_4$, 14 µM $MnCl_2$, 1.6 µM $CuSO_4$, 0.86 µM $CoCl_2$, 1.9 µM boric acid, 5.5 µM $NiCl_2$, 6.72 µM EDTA, 0.6% glycerol). 4 mL of this culture was then taken in a 15 mL borosilicate glass tube, to which riluzole analogs in DMSO were added to a final concentration of 200 µM (for the control experiments, same amount of DMSO was added). These cultures were then grown for 20 h at 37° C. and 200 RPM. The final $OD_{620}$ was measured, and the cells were pelleted at 5000 g for 5 min. 1 mL of the supernatant was taken and extracted twice with 1 mL of diethyl ether. The pooled organic extracts were dried over anhydrous magnesium sulfate, evaporated to dryness and then reconstituted in 200 µL deionized water. Then, 50 µL of this extract was diluted into 450 µL of a solution of 0.19% (w/v) orcinol in 50% (v/v) concentrated $H_2SO_4$. The tubes were briefly vortexed and incubated in an 80° C. heating block for 45 min. After briefly cooling to room temperature, 200 µL of the resulting solution was transferred to a clear 96-well microtiter plate and the absorbance at 421 nm measured. Data were normalized to the final $OD_{620}$ values and plotted relative to a DMSO control.

Figure 8:
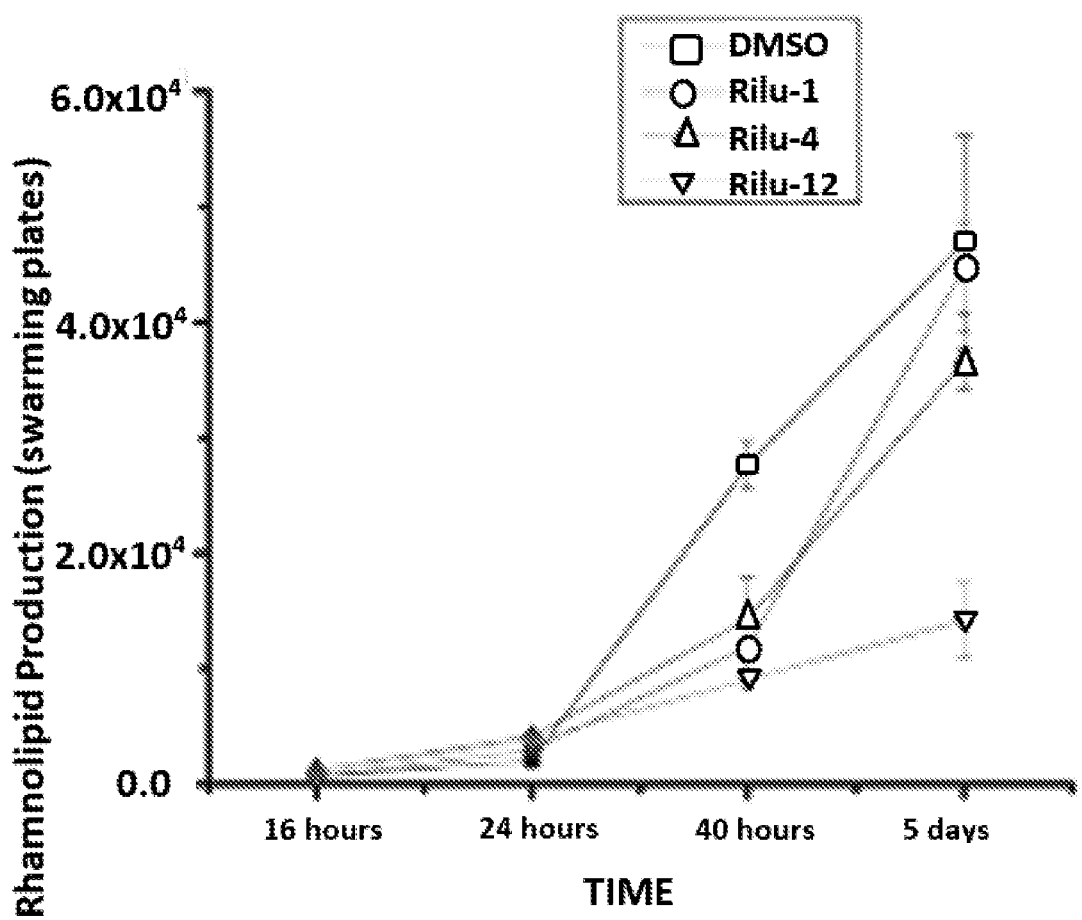
FIG. 8 is a graph showing production of rhamnolipids in cultures of *P. aeruginosa* strain PA14.

FIG. 8 is a graph showing production of rhamnolipids in cultures of P. aeruginosa strain PA14. As seen in FIG. 8, RL production was lowest in the presence of Rilu-12 (70% reduction). The loss of swarming behavior indicates that the motility machinery and surfactant production are significantly affected by the riluzole analogs.

Example 10

The dose dependence inhibitory activity of riluzole analogs was analyzed using an activity-based probe BODIPY-FL-ATPγS (B-ATPγS). BODIPY-ATPγS competition screening was performed at inhibitor concentrations that did not cause aggregation. Triton X-100 was premixed with reaction buffer to yield 0.1% (v/v) in final 25-μL reactions. In reaction buffer, 1 μM HK853 was preincubated with test compounds (final concentration, 0.01-1250 μM) in 24 μL for 30 min. 1 μL BODIPY-ATPγS was added to bring the final 25-μL reactions to 0.96 μM HK853 and 2 μM BODIPY-ATPγS in the presence of competitors and 5% DMSO. Samples were mixed and incubated in the dark at RT for 1 h before quenching with 8.6 μL 4×SDS-PAGE sample loading buffer and loading 15 μL on a 10% stacking gel. After SDS-PAGE, in-gel fluorescence detection elucidated HK853 activity, and coomassie staining of the gels ensured even protein loading. Integrated density values of the fluorescent gel bands were normalized as "% Activity" with respect to a control that contained no inhibitor. Data were plotted in GraphPad Prism (version 7.0 for Mac, GraphPad Software, San Diego, Calif. USA, www.graphpad.com) with relation to the log of molar inhibitor to determine $IC_{50}$ values, shown in TABLE 3, by fitting the dose-response curves to EQUATION 1. While compounds Rilu-1, Rilu-2, Rilu-3, Rilu-4, Rilu-5, Rilu-6, Rilu-7, Rilu-8, Rilu-9, and Rilu-12 were found to inhibit HKs, compounds Rilu-10 and Rilu-11 did not significantly inhibit HKs. The structures of Rilu-10 and Rilu-11 are given by:

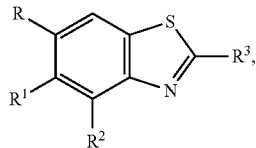

where R=Cl, $R^L$=H, $R^2$=Cl, $R^3$=NH$_2$ (Rilu-10); where R=Br, $R^1$=Br, $R^2$=H, $R^3$=NH$_2$ (Rilu-11).

TABLE 3

| Cmpd # | IC$_{50}$ values (μM) (95% confidence interval), n = 2 | Cmpd # | IC$_{50}$ values (μM) (95% confidence interval), n = 2 |
|---|---|---|---|
| Rilu-1 | 7.15 μM | Rilu-2 | 1.21 μM |
| Rilu-3 | 86.4 (5.81 to 128.3) | Rilu-8 | 77.4 (50.7 to 118.1) |
| Rilu-4 | 8.30 (7.27 to 9.47) | Rilu-9 | 161 (88.15 to 295.6) |
| Rilu-5 | 97.5 (57.5 to 165.2) | Rilu-10 | No Inhibition |
| Rilu-6 | 15.1 (9.98 to 22.7) | Rilu-11 | No Inhibition |
| Rilu-7 | 1394 (150 to 12940) | Rilu-12 | 1.56 (1.17 to 2.06) |

Comparative Example 1

The inhibition of HK853 by non-native bases or nucleosides was evaluated. Guanine, Guanosine, and Inosine did not appear to inhibit HK853. Hypoxanthine ($IC_{50}$=1.2 mM) and 8-azadenine ($IC_{50}$>2 mM) had relatively low affinity for HK853. 8-azadenine has an additional N at C-8, and it appeared that providing this additional N prevented 8-azadenine from binding to HK853.

Clause 1: A composition including a therapeutically effective amount of a histidine kinase inhibitor for treating a bacterial infection, wherein the histidine kinase inhibitor comprises at least one of a 6-benzo[d]thiazol-2-amine derivative, a purine derivative, an adenine derivative, an adenine-sulfonyl fluoride derivative, a riluzole analog, a riluzole-sulfonyl fluoride derivative, a 6-benzo[d]thiazol-2-amine-sulfonyl fluoride derivative, a 6,6'-oxybis(benzo[d]thiazol-2-amine) derivative, or a 6,6'-oxybis(benzo[d]thiazol-2-amine)-sulfonyl fluoride derivative.

Clause 2: The composition of clause 1, wherein the 6-benzo[d]thiazol-2-amine derivative comprises a compound having a structure

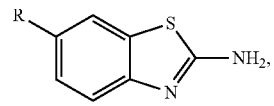

where R=CH$_3$, Cl, NO$_2$, OCH$_3$, or CF$_3$.

Clause 3: The composition of clause 1, wherein the purine derivative comprises a compound having a structure chosen from:

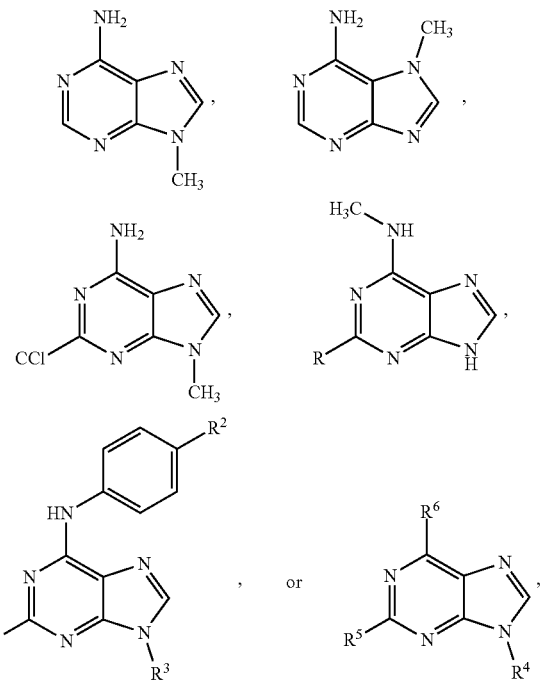

where R=H or Cl, $R^1$=H or Cl, $R^2$=H, C, or F, $R^3$=H or ribose, $R^4$=H or ribose, $R^5$=H, NH$_2$, Cl, or F, and $R^6$=H, Cl, or NH$_2$.

Clause 4: The composition of clause 1, wherein the adenine-sulfonyl fluoride derivative comprises a compound having a structure chosen from:

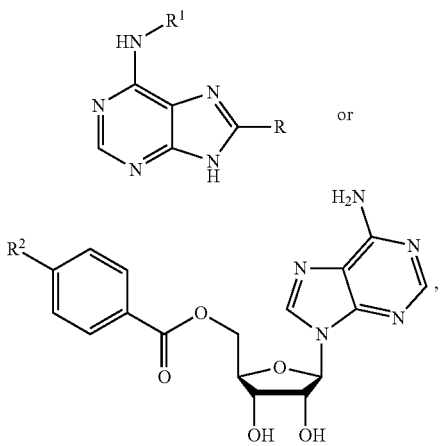

where R=H or

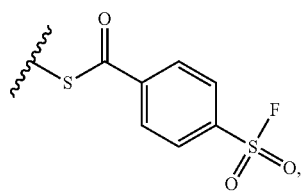 [SMILES: *SC(=O)c1ccc(S(=O)(=O)F)cc1]

R¹=H or

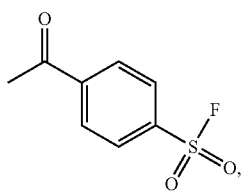

and R²=H, SO₃H, or SO₂F.

Clause 5: The composition of clause 1, wherein the 6,6'-oxybis(benzo[d]thiazol-2-amine) derivative comprises a compound having a structure

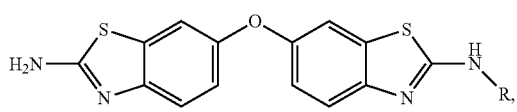

where R=COCH₃ or

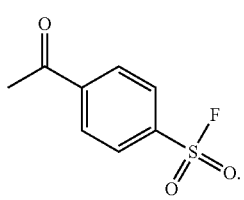

Clause 6: The composition of any one of clauses 1 to 5, wherein the riluzole analog comprises a compound having a structure chosen from:

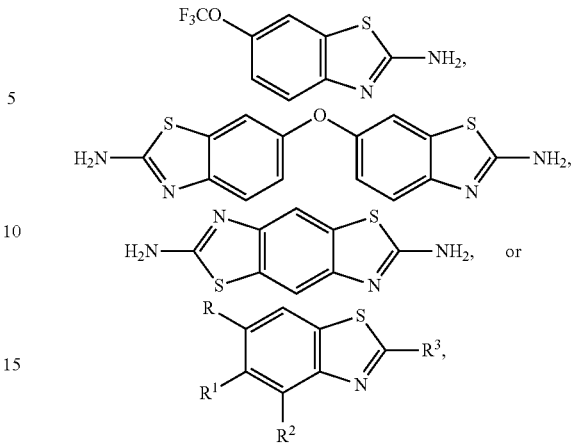

where R=CH₃, R¹=H, R²=H, R³=NH₂; or R=NO₂, R¹=H, R²=H, R³=NH₂; or R=Cl, R₁=H, R²=H, R³=NH₂; or R=CF₃, R¹=H, R²=H, R³=NH₂; or R=NH₂, R¹=H, R²=H, R³=CH₃; or R=OCH₃, R¹=H, R²=H, R³=NH₂; or R=NH₂, R¹=H, R²=H, R³=NH₂; or R=NHCH₂-arylsulfonyl fluoride, R¹=H, R²=H, R³=NH₂; or R=NHC(O)-arylsulfonyl fluoride, R¹=H, R²=H, R³=NH₂.

Clause 7: The composition of any of clauses 1 to 6, wherein the histidine kinase inhibitor inhibits at least one bacterial histidine kinase.

Clause 8: The composition of clause 7, wherein the at least one bacterial histidine kinase comprises at least one of a gram-positive bacterial histidine kinase, a gram-negative bacterial histidine kinase, histidine kinase HK853, histidine kinase VicK, histidine kinase CheA, histidine kinase PhoQ, or histidine kinase WigK.

Clause 9: The composition of any of clauses 1 to 8, wherein the histidine kinase inhibitor is an antibiotic or an antibacterial agent.

Clause 10: The composition of any of clauses 1 to 9, wherein the composition comprises 0.01%, 0.1%, 1%, 2%, 5%, or 10% (weight/weight) of the histidine kinase inhibitor.

Clause 11: The composition of any of clauses 1 to 10, including a
pharmaceutically acceptable carrier.

Clause 12: The composition of clause 11, wherein the pharmaceutically acceptable carrier comprises one or more of a cream, a lotion, a spray, a gel, an ointment, a paste, a solution, a suspension, an emulsion, a powder, a liquid, or a solid.

Clause 13: A formulation including the composition of any one of clauses 1 to 12, wherein the formulation is topical, injectable, parenteral, or oral.

Clause 14: A method including administering the composition of any one of clauses 1 to 13 to a patient suffering from bacterial infection.

Clause 15: The method of clause 14, wherein administering the composition comprises administering at least 0.1 mg/day, 1 mg/day, 5 mg/day, 10 mg/day, 20 mg/day, 50 mg/day, or 100 mg/day of the histidine kinase inhibitor.

Clause 16: The method of clause 15 or further, further including administering a co-antibiotic to the patient.

Various examples have been described. These and other examples are within the scope of the following claims.

What is claimed is:

1. A composition comprising a therpeutically effective amount of a histidine kinase inhibitor for treating a bacterial infection, wherein the histidine kinase inhibitor comprises a riluzole analog having a structure

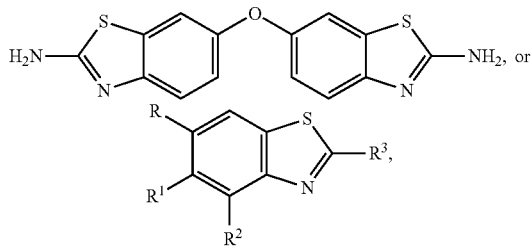

where R=Cl, $R^1$=H, $R^2$=H, $R^3$=NH$_2$; or R=CF$_3$, $R^1$=H, $R^2$=H, $R^3$=NH$_2$; or R=NH$_2$, $R^1$=H, $R^2$=H, $R^3$=CH$_3$; or R=OCH$_3$, $R^1$=H, $R^2$=H, $R^3$=NH$_2$; or R=NH$_2$, $R^1$=H, $R^2$=H, $R^3$=NH$_2$; or R=NHCH$_2$-arylsulfonyl fluoride, $R^1$=H, $R^2$=H, $R^3$=NH$_2$; or R=NHC(O)-arylsufonyl fluoride, $R^1$=H, $R^2$=H, $R^3$=NH$_2$.

2. A composition comprising a therapeutically effective amount of a histidine kinase inhibitor for treating a bacterial infection, wherein the histidine kinase inhibitor comprises a 6-benzo[d]thiazol-2-amine derivative having a structure

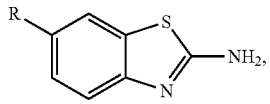

where R=Cl, OCH$_3$, or CF$_3$.

3. A composition comprising a therapeutically effective amount of a histidine kinase inhibitor for treating a bacterial infection, wherein the histidine kinase inhibitor comprises a 6,6'-oxybis(benzo[d]thiazol-2-amine) derivative having a structure

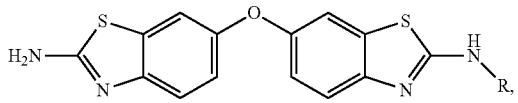

where R=COCH$_3$ or

4. The composition of claim 1, wherein the composition comprises 0.01%, 0.1%, 1%, 2%, 5%, or 10% (weight/weight) of the histidine kinase inhibitor.

5. The composition of claim 1, comprising a pharmaceutically acceptable carrier.

6. The composition of claim 5, wherein the pharmaceutically acceptable carrier comprises one or more of a cream, a lotion, a spray, a gel, an ointment, a paste, a solution, a suspension, an emulsion, a powder, a liquid, or a solid.

7. A formulation comprising the composition of claim 1, wherein the formulation is topical, injectable, parenteral, or oral.

8. The composition of claim 2, wherein the composition comprises 0.01%, 0.1%, 1%, 2%, 5%, or 10% (weight/weight) of the histidine kinase inhibitor.

9. The composition of claim 2, comprising a pharmaceutically acceptable carrier.

10. The composition of claim 9, wherein the pharmaceutically acceptable carrier comprises one or more of a cream, a lotion, a spray, a gel, an ointment, a paste, a solution, a suspension, an emulsion, a powder, a liquid, or a solid.

11. A formulation comprising the composition of claim 2, wherein the formulation is topical, injectable, parenteral, or oral.

12. The composition of claim 3, wherein the composition comprises 0.01%, 0.1%, 1%, 2%, 5%, or 10% (weight/weight) of the histidine kinase inhibitor.

13. The composition of claim 3, comprising a pharmaceutically acceptable carrier.

14. The composition of claim 13, wherein the pharmaceutically acceptable carrier comprises one or more of a cream, a lotion, a spray, a gel, an ointment, a paste, a solution, a suspension, an emulsion, a powder, a liquid, or a solid.

15. A formulation comprising the composition of claim 3, wherein the formulation is topical, injectable, parenteral, or oral.

* * * * *

UNITED STATES PATENT AND TRADEMARK OFFICE
CERTIFICATE OF CORRECTION

PATENT NO. : 11,452,714 B2
APPLICATION NO. : 16/615585
DATED : September 27, 2022
INVENTOR(S) : Erin E. Carlson and Manibarsha Goswami Page 1 of 1

It is certified that error appears in the above-identified patent and that said Letters Patent is hereby corrected as shown below:

In the Claims

Column 23, Claim 1, Lines 8-11 Replace:

" 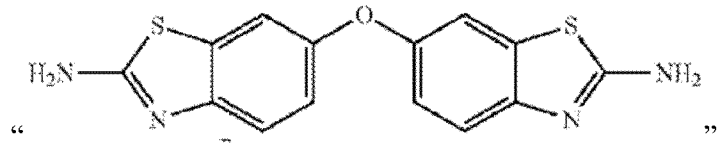 ,"

With:

-- 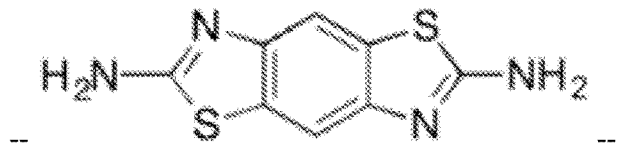 --

Signed and Sealed this
Twentieth Day of February, 2024

Katherine Kelly Vidal
*Director of the United States Patent and Trademark Office*